(12) United States Patent
Deisseroth et al.

(10) Patent No.: US 10,018,695 B2
(45) Date of Patent: *Jul. 10, 2018

(54) OPTOGENETIC MAGNETIC RESONANCE IMAGING

(71) Applicant: The Board of Trustees of the Leland Stanford Junior University, Stanford, CA (US)

(72) Inventors: Karl Deisseroth, Stanford, CA (US); Jin Hyung Lee, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/425,925

(22) Filed: Feb. 6, 2017

(65) Prior Publication Data

US 2017/0160360 A1 Jun. 8, 2017

Related U.S. Application Data

(63) Continuation of application No. 15/008,214, filed on Jan. 27, 2016, now Pat. No. 9,615,789, which is a
(Continued)

(51) Int. Cl.
*A61N 5/06* (2006.01)
*G01R 33/48* (2006.01)
(Continued)

(52) U.S. Cl.
CPC ........ *G01R 33/4806* (2013.01); *A61B 5/0042* (2013.01); *A61B 5/055* (2013.01);
(Continued)

(58) Field of Classification Search
CPC ........ A61N 5/06; A61N 5/0601; A61N 5/062; A61N 5/0622; A61N 5/0616
(Continued)

(56) References Cited

U.S. PATENT DOCUMENTS

| 2,968,302 A | 1/1961 | Fry et al. |
| 3,131,690 A | 5/1964 | Innis et al. |

(Continued)

FOREIGN PATENT DOCUMENTS

| CN | 1079464 A | 12/1993 |
| CN | 1558222 A | 12/2004 |

(Continued)

OTHER PUBLICATIONS

Co-pending U.S. Appl. No. 15/334,007, filed Oct. 25, 2016.
(Continued)

*Primary Examiner* — John R Downey
(74) *Attorney, Agent, or Firm* — Bozicevic, Field & Francis LLP; Paula A. Borden; Rudy J. Ng

(57) ABSTRACT

Disclosed herein are systems and methods involving the use of magnetic resonance imaging and optogenetic neural stimulation. Aspects of the disclosure include modifying a target neural cell population in a first region of a brain to express light-responsive molecules. Using a light pulse, the light-responsive molecules in the target neural cell population are stimulated. Multiple regions of the brain are scanned via magnetic resonance imaging. The scans allow for observation of a neural reaction in response to the stimulation in at least one of the multiple regions of the brain.

15 Claims, 12 Drawing Sheets

Related U.S. Application Data continuation of application No. 14/298,413, filed on Jun. 6, 2014, now Pat. No. 9,271,674, which is a continuation of application No. 13/847,653, filed on Mar. 20, 2013, now Pat. No. 8,834,546, which is a continuation of application No. 13/299,727, filed on Nov. 18, 2011, now Pat. No. 8,696,722.

(60) Provisional application No. 61/416,143, filed on Nov. 22, 2010.

(51) Int. Cl.
    *A61B 5/00*           (2006.01)
    *A61B 5/055*         (2006.01)

(52) U.S. Cl.
    CPC .......... *A61B 5/4848* (2013.01); *A61N 5/0622* (2013.01); *G01R 33/4808* (2013.01)

(58) Field of Classification Search
    USPC .......................... 607/80, 90; 604/21; 514/44
    See application file for complete search history.

(56) References Cited

U.S. PATENT DOCUMENTS

| | | | |
|---|---|---|---|
| 3,499,437 A | 3/1970 | Balamuth et al. | |
| 3,567,847 A | 3/1971 | Price | |
| 4,343,301 A | 8/1982 | Indech | |
| 4,559,951 A | 12/1985 | Dahl et al. | |
| 4,616,231 A | 10/1986 | Autrey et al. | |
| 4,865,042 A | 9/1989 | Umemura et al. | |
| 4,879,284 A | 11/1989 | Lang et al. | |
| 5,032,123 A | 7/1991 | Katz et al. | |
| 5,041,224 A | 8/1991 | Ohyama et al. | |
| 5,082,670 A | 1/1992 | Gage et al. | |
| 5,249,575 A | 10/1993 | Di Miro et al. | |
| 5,267,152 A | 11/1993 | Yang et al. | |
| 5,290,280 A | 3/1994 | Daikuzono et al. | |
| 5,330,515 A | 7/1994 | Rutecki et al. | |
| 5,382,516 A | 1/1995 | Bush | |
| 5,411,540 A | 5/1995 | Edell et al. | |
| 5,445,608 A | 8/1995 | Chen et al. | |
| 5,460,950 A | 10/1995 | Barr et al. | |
| 5,460,954 A | 10/1995 | Lee et al. | |
| 5,470,307 A | 11/1995 | Lindall | |
| 5,495,541 A | 2/1996 | Murray et al. | |
| 5,520,188 A | 5/1996 | Hennige et al. | |
| 5,527,695 A | 6/1996 | Hodges et al. | |
| 5,550,316 A | 8/1996 | Mintz | |
| 5,641,650 A | 6/1997 | Turner et al. | |
| 5,703,985 A | 12/1997 | Owyang et al. | |
| 5,722,426 A | 3/1998 | Kolff | |
| 5,738,625 A | 4/1998 | Gluck | |
| 5,739,273 A | 4/1998 | Engelman et al. | |
| 5,741,316 A | 4/1998 | Chen et al. | |
| 5,755,750 A | 5/1998 | Petruska et al. | |
| 5,756,351 A | 5/1998 | Isacoff et al. | |
| 5,782,896 A | 7/1998 | Chen et al. | |
| 5,795,581 A | 8/1998 | Segalman et al. | |
| 5,807,285 A | 9/1998 | Vaitekunas et al. | |
| 5,816,256 A | 10/1998 | Kissinger et al. | |
| 5,836,941 A | 11/1998 | Yoshihara et al. | |
| 5,898,058 A | 4/1999 | Nichols | |
| 5,939,320 A | 8/1999 | Littman et al. | |
| 6,056,738 A | 5/2000 | Marchitto et al. | |
| 6,057,114 A | 5/2000 | Akong | |
| 6,108,081 A | 8/2000 | Holtom et al. | |
| 6,134,474 A | 10/2000 | Fischell et al. | |
| 6,161,045 A | 12/2000 | Fischell et al. | |
| 6,180,613 B1 | 1/2001 | Kaplitt et al. | |
| 6,253,109 B1 | 6/2001 | Gielen | |
| 6,303,362 B1 | 10/2001 | Kay et al. | |
| 6,334,846 B1 | 1/2002 | Ishibashi et al. | |
| 6,336,904 B1 | 1/2002 | Nikolchev | |
| 6,346,101 B1 | 2/2002 | Alfano et al. | |
| 6,364,831 B1 | 4/2002 | Crowley | |
| 6,377,842 B1 | 4/2002 | Pogue et al. | |
| 6,436,708 B1 | 8/2002 | Leone et al. | |
| 6,473,639 B1 | 10/2002 | Fischell et al. | |
| 6,480,743 B1 | 11/2002 | Kirkpatrick et al. | |
| 6,489,115 B2 | 12/2002 | Lahue et al. | |
| 6,497,872 B1 | 12/2002 | Weiss et al. | |
| 6,506,154 B1 | 1/2003 | Ezion et al. | |
| 6,536,440 B1 | 3/2003 | Dawson | |
| 6,551,346 B2 | 4/2003 | Crossley | |
| 6,567,690 B2 | 5/2003 | Giller et al. | |
| 6,597,954 B1 | 7/2003 | Pless et al. | |
| 6,609,020 B2 | 8/2003 | Gill | |
| 6,615,080 B1 | 9/2003 | Unsworth et al. | |
| 6,631,283 B2 | 10/2003 | Storrie et al. | |
| 6,632,672 B2 | 10/2003 | Calos | |
| 6,647,296 B2 | 11/2003 | Fischell et al. | |
| 6,685,656 B1 | 2/2004 | Duarte et al. | |
| 6,686,193 B2 | 2/2004 | Maher et al. | |
| 6,721,603 B2 | 4/2004 | Zabara et al. | |
| 6,729,337 B2 | 5/2004 | Dawson | |
| 6,780,490 B1 | 8/2004 | Tanaka et al. | |
| 6,790,652 B1 | 9/2004 | Terry et al. | |
| 6,790,657 B1 | 9/2004 | Arya | |
| 6,805,129 B1 | 10/2004 | Pless et al. | |
| 6,808,873 B2 | 10/2004 | Murphy et al. | |
| 6,810,285 B2 | 10/2004 | Pless et al. | |
| 6,889,085 B2 | 5/2005 | Dawson | |
| 6,918,872 B2 | 7/2005 | Yokoi | |
| 6,921,413 B2 | 7/2005 | Mahadevan-Jansen et al. | |
| 6,969,449 B2 | 11/2005 | Maher et al. | |
| 6,974,448 B2 | 12/2005 | Petersen | |
| 7,045,344 B2 | 5/2006 | Kay et al. | |
| 7,091,500 B2 | 8/2006 | Schnitzer | |
| 7,144,733 B2 | 12/2006 | Miesenbock et al. | |
| 7,175,596 B2 | 2/2007 | Vitek et al. | |
| 7,191,018 B2 | 3/2007 | Gielen et al. | |
| 7,211,054 B1 | 5/2007 | Francis et al. | |
| 7,220,240 B2 | 5/2007 | Struys et al. | |
| 7,298,143 B2 | 11/2007 | Jaermann et al. | |
| 7,313,442 B2 | 12/2007 | Velasco et al. | |
| 7,603,174 B2 | 10/2009 | De Ridder | |
| 7,610,100 B2 | 10/2009 | Jaax et al. | |
| 7,613,520 B2 | 11/2009 | De Ridder | |
| 7,686,839 B2 | 3/2010 | Parker | |
| 7,824,869 B2 | 11/2010 | Hegemann et al. | |
| 7,883,536 B1 | 2/2011 | Bendett | |
| 7,988,688 B2 | 8/2011 | Webb et al. | |
| 8,386,312 B2 | 2/2013 | Pradeep et al. | |
| 8,398,692 B2 | 3/2013 | Deisseroth et al. | |
| 8,401,609 B2 | 3/2013 | Deisseroth et al. | |
| 8,603,790 B2 | 12/2013 | Deisseroth et al. | |
| 8,696,722 B2 | 4/2014 | Deisseroth et al. | |
| 8,716,447 B2 | 5/2014 | Deisseroth et al. | |
| 8,729,040 B2 | 5/2014 | Deisseroth et al. | |
| 8,815,582 B2 | 8/2014 | Deisseroth et al. | |
| 8,834,546 B2 | 9/2014 | Deisseroth et al. | |
| 8,864,805 B2 | 10/2014 | Deisseroth et al. | |
| 8,906,360 B2 | 12/2014 | Deisseroth et al. | |
| 8,926,959 B2 | 1/2015 | Deisseroth et al. | |
| 8,932,562 B2 | 1/2015 | Deisseroth et al. | |
| 8,956,363 B2 | 2/2015 | Deisseroth et al. | |
| 8,962,589 B2 | 2/2015 | Deisseroth et al. | |
| 9,057,734 B2 | 6/2015 | Cohen | |
| 9,079,940 B2 | 7/2015 | Deisseroth et al. | |
| 9,084,885 B2 | 7/2015 | Deisseroth et al. | |
| 9,101,690 B2 | 8/2015 | Deisseroth et al. | |
| 9,101,759 B2 | 8/2015 | Deisseroth et al. | |
| 9,175,095 B2 | 11/2015 | Deisseroth et al. | |
| 9,187,745 B2 | 11/2015 | Deisseroth et al. | |
| 9,238,150 B2 | 1/2016 | Deisseroth et al. | |
| 9,249,200 B2 | 2/2016 | Deisseroth et al. | |
| 9,249,234 B2 | 2/2016 | Deisseroth et al. | |
| 9,271,674 B2 | 3/2016 | Deisseroth et al. | |
| 9,274,099 B2 | 3/2016 | Deisseroth et al. | |
| 9,278,159 B2 | 3/2016 | Deisseroth et al. | |
| 9,284,353 B2 | 3/2016 | Deisseroth et al. | |
| 9,308,392 B2 | 4/2016 | Deisseroth et al. | |

(56) References Cited

U.S. PATENT DOCUMENTS

| | | |
|---|---|---|
| 9,309,296 B2 | 4/2016 | Deisseroth et al. |
| 9,340,589 B2 | 5/2016 | Deisseroth et al. |
| 9,359,449 B2 | 6/2016 | Deisseroth et al. |
| 9,360,472 B2 | 6/2016 | Deisseroth et al. |
| 9,365,628 B2 | 6/2016 | Deisseroth et al. |
| 9,394,347 B2 | 7/2016 | Deisseroth et al. |
| 9,458,208 B2 | 10/2016 | Deisseroth et al. |
| 9,522,288 B2 | 12/2016 | Deisseroth et al. |
| 9,604,073 B2 | 3/2017 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0267118 A1 | 12/2004 | Dawson |
| 2005/0020945 A1 | 1/2005 | Tosaya et al. |
| 2005/0058987 A1 | 3/2005 | Shi et al. |
| 2005/0088177 A1* | 4/2005 | Schreck ............... A61B 5/055 324/307 |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | de Charms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Iyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0046053 A1 | 1/2008 | Wagner et al. |
| 2008/0033569 A1 | 2/2008 | Ferren et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0103551 A1 | 5/2008 | Masoud et al. |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0131837 A1 | 5/2009 | Granville |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs et al. |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Deisseroth et al. |
| 2010/0209352 A1 | 8/2010 | Hultman et al. |
| 2010/0234273 A1 | 9/2010 | Deisseroth et al. |
| 2011/0221970 A1 | 1/2011 | Vo-Dihn et al. |
| 2011/0092800 A1 | 4/2011 | Yoo et al. |
| 2011/0105998 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |

(56) References Cited

U.S. PATENT DOCUMENTS

| | | |
|---|---|---|
| 2011/0165681 A1 | 7/2011 | Boyden et al. |
| 2011/0166632 A1 | 7/2011 | Delp et al. |
| 2011/0233046 A1 | 9/2011 | Nikolenko et al. |
| 2011/0301529 A1 | 12/2011 | Deisseroth et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0253261 A1 | 10/2012 | Poletto et al. |
| 2013/0030275 A1 | 1/2013 | Seymour et al. |
| 2013/0144359 A1 | 6/2013 | Kishawi et al. |
| 2013/0284920 A1 | 10/2013 | Deisseroth et al. |
| 2013/0286181 A1 | 10/2013 | Betzig et al. |
| 2013/0289669 A1 | 10/2013 | Deisseroth et al. |
| 2013/0317569 A1 | 11/2013 | Deisseroth et al. |
| 2013/0317575 A1 | 11/2013 | Deisseroth et al. |
| 2013/0330816 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0082758 A1 | 3/2014 | Deisseroth et al. |
| 2014/0148880 A1 | 5/2014 | Deisseroth et al. |
| 2014/0235826 A1 | 8/2014 | Deisseroth et al. |
| 2014/0271479 A1 | 9/2014 | Lammel et al. |
| 2014/0324133 A1 | 10/2014 | Deisseroth et al. |
| 2015/0040249 A1 | 2/2015 | Deisseroth et al. |
| 2015/0112411 A1 | 4/2015 | Beckman et al. |
| 2015/0165227 A1 | 6/2015 | Deisseroth et al. |
| 2015/0174244 A1 | 6/2015 | Deisseroth et al. |
| 2015/0217128 A1 | 8/2015 | Deisseroth et al. |
| 2015/0218547 A1 | 8/2015 | Deisseroth et al. |
| 2016/0015996 A1 | 1/2016 | Deisseroth et al. |
| 2016/0038761 A1 | 2/2016 | Deisseroth et al. |
| 2016/0038764 A1 | 2/2016 | Deisseroth et al. |
| 2016/0045599 A1 | 2/2016 | Deisseroth et al. |
| 2016/0096036 A1 | 4/2016 | Deisseroth et al. |
| 2016/0175607 A1 | 6/2016 | Deisseroth et al. |
| 2016/0194624 A1 | 7/2016 | Deisseroth et al. |
| 2016/0199663 A1 | 7/2016 | Deisseroth et al. |
| 2016/0222073 A1 | 8/2016 | Deisseroth et al. |

FOREIGN PATENT DOCUMENTS

| | | |
|---|---|---|
| CN | 102076866 A | 5/2011 |
| CN | 103313752 A | 9/2013 |
| CN | 103476456 A | 12/2013 |
| EP | 1197144 | 4/2002 |
| EP | 1334748 | 8/2003 |
| EP | 1444889 | 8/2004 |
| EP | 1873566 | 1/2008 |
| JP | 6295350 | 10/1994 |
| JP | H 09505771 A | 6/1997 |
| JP | 2004534508 | 11/2004 |
| JP | 2005034073 A | 2/2005 |
| JP | 2007530027 A | 11/2007 |
| JP | 2008010422 A | 1/2008 |
| JP | 2010227537 A | 10/2010 |
| JP | 2012508581 | 4/2012 |
| WO | WO 1995/005214 | 2/1995 |
| WO | WO 1996/032076 | 10/1996 |
| WO | WO 2000/027293 | 5/2000 |
| WO | WO 2001/025466 | 4/2001 |
| WO | WO 2003/016486 | 2/2003 |
| WO | WO 2003/040323 | 5/2003 |
| WO | WO 2003/046141 | 6/2003 |
| WO | WO 2003/084994 | 10/2003 |
| WO | WO 2003/102156 | 12/2003 |
| WO | WO 2004/033647 | 4/2004 |
| WO | WO 2005/093429 | 10/2005 |
| WO | WO 2006/103678 | 10/2006 |
| WO | WO 2007/024391 | 3/2007 |
| WO | WO 2007/131180 | 11/2007 |
| WO | WO 2008/014382 | 1/2008 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO 2009/119782 | 10/2009 |
| WO | WO 2009/131837 | 10/2009 |
| WO | WO 2009/148946 | 12/2009 |
| WO | WO 2010/006049 | 1/2010 |
| WO | WO 2010/011404 | 1/2010 |
| WO | WO 2010/056970 | 5/2010 |
| WO | WO 2010/123993 | 10/2010 |
| WO | WO 2011/005978 | 1/2011 |
| WO | WO 2011/066320 | 6/2011 |
| WO | WO 2011/106783 | 9/2011 |
| WO | WO 2011/116238 | 9/2011 |
| WO | WO 2011/127088 | 10/2011 |
| WO | WO 2012/032103 | 3/2012 |
| WO | WO 2012/061676 | 5/2012 |
| WO | WO 2012/061681 | 5/2012 |
| WO | WO 2012/061684 | 5/2012 |
| WO | WO 2012/061688 | 5/2012 |
| WO | WO 2012/061690 | 5/2012 |
| WO | WO 2012/061741 | 5/2012 |
| WO | WO 2012/061744 | 5/2012 |
| WO | WO 2012/106407 | 8/2012 |
| WO | WO 2012/134704 | 10/2012 |
| WO | WO 2013/003557 | 1/2013 |
| WO | WO 2013/016486 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2016/019075 | 2/2016 |

OTHER PUBLICATIONS

Co-pending U.S. Appl. No. 15/008,214, filed Jan. 27, 2016.
Co-pending U.S. Appl. No. 15/095,159, filed Mar. 2, 2016.
Co-pending U.S. Appl. No. 15/095,519, filed Apr. 11, 2016.
Co-pending U.S. Appl. No. 15/147,772, filed May 5, 2016.
Co-pending U.S. Appl. No. 15/153,299, filed May 12, 2016.
Co-pending U.S. Appl. No. 15/153,305, filed May 12, 2016.
Co-pending U.S. Appl. No. 15/156,124, filed May 16, 2016.
Co-pending U.S. Appl. No. 15/194,379, filed Jun. 27, 2016.
Co-pending U.S. Appl. No. 15/214,399, filed Jul. 19, 2016.
Co-pending U.S. Appl. No. 15/214,400, filed Jul. 19, 2016.
Co-pending U.S. Appl. No. 15/214,402, filed Jul. 19, 2016.
Co-pending U.S. Appl. No. 15/214,403, filed Jul. 19, 2016.
Co-pending U.S. Appl. No. 15/229,064, filed Aug. 4, 2016.
Co-pending U.S. Appl. No. 15/351,067, filed Nov. 14, 2016.
Co-pending U.S. Appl. No. 15/126,859, filed Sep. 16, 2016.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Ahmad, et al. "The *Drosophila rhodopsin* cytoplasmic tail domain is required for maintenance of rhabdomere structure." The FASEB Journal, 2007, vol. 21, p. 449-455.
Airan, et al.; "Integration of light-controlled neuronal firing and fast circuit imaging"; Current Opinion in Neurobiology; vol. 17, pp. 587-592 (2007).
Airan, et al., "Temporally Precise in vivo Control of Intracellular Signaling", 2009, Nature, vol. 458, No. 7241, pp. 1025-1029.
Akirav, et al. "The role of the medial prefrontal cortex-amygdala circuit in stress effects on the extinction of fear", Neural Plasticity, 2007: vol. 2007 Article ID:30873, pp. 1-11.
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).

(56) References Cited

OTHER PUBLICATIONS

Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the cre Gene Mediated by Cre Recombinase Using a Combination of Mutant lox Sites", Nucleic Acids Research, 2002, vol. 30, No. 19, pp. 1-8.
Aravanis, et al. "An optical neural interface: in vivo control of rodent motor cortex with integrated fiberoptic and optogenetic technology," J. Neural. Eng., 2007, vol. 4(3):S143-S156.
Arenkiel, et al. "In vivo light-induced activation of neural circuitry in transgenic mice expressing Channelrhodopsin-2", Neuron, 2007, 54:205-218.
Argos, et al. "The integrase family of site-specific recombinases: regional similarities and global diversity", The EMBO Journal, 1986, vol. 5, No. 2, pp. 433-440.
Asano, et al.; "Optically Controlled Contraction of Photosensitive Skeletal Muscle Cells"; Biotechnology & Bioengineering; vol. 109, No. 1, pp. 199-204 (Jan. 2012).
Axoclamp-2B Microelectrode claim theory and operation. Accessed from https://physics.ucsd.edu/neurophysics/Manuals/Axon%20Instruments/Axoclamp-2B_Manual.pdf on Dec. 12, 2014.
Babin et al., "Zebrafish Models of Human Motor Neuron Diseases: Advantages and Limitations", Progress in Neurobiology (2014), 118:36-58.
Balint et al., "The Nitrate Transporting Photochemical Reaction Cycle of the Pharanois Halorhodopsin", Biophysical Journal, 2004, 86:1655-1663.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Basil et al.; "Is There Evidence for Effectiveness of Transcranial Magnetic Stimulation in the Treatment of Psychiatric Disorders?"; Psychiatry; vol. 1, No. 11, pp. 64-69 (Nov. 2005).
Bebbington et al., "The use of vectors based on gene amplification for the expression of cloned genes in mammalian cells in DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berke, et al. "Addiction, Dopamine, and the Molecular Mechanisms of Memory", Molecular Plasticity, 2000, vol. 25: pp. 515-532.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Berndt et al. "Bi-stable neural state switches", Nature Neuroscience, 2008, vol. 12, No. 2: pp. 229-234.
Berndt et al., "Structure-guided transformation of channelrhodopsin into a light-activated chloride channel", Science, 2014, 344:420-424.
Berridge et al., "The Versatility and Universality of Calcium Signaling", Nature Reviews: Molecular Cell Biology, 2000, vol. 1: pp. 11-21.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-10472.
Blomer et al., "Highly Efficient and Sustained Gene Transfer in Adult Neurons with Lentivirus Vector", Journal of Virology,1997, vol. 71, No. 9: pp. 6641-6649.
Bocquet et al. "A prokaryotic proton-gated ion channel from the nicotinic acetylcholine receptor family." Nature Letters, 2007, vol. 445, p. 116-119.
Bowers, et al.; "Genetic therapy for the nervous system"; Human Molecular Genetics; vol. 20, No. 1, pp. R28-R41 (2011).
Boyden, et al. "Millisecond-timescale, genetically targeted optical control of neural activity" Nature Neuroscience, 2005, vol. 8, No. 9: pp. 1263-1268.
Braun, "Two Light-activated Conductances in the Eye of the Green Alga *Volvox carteri*", 1999, Biophys J., vol. 76, No. 3, pp. 1668-1678.
Brewin; "The Nature and Significance of Memory Disturbance in Posttraumatic Stress Disorder"; Ann. Rev. Clin. Psychol.; vol. 7, pp. 203-227 (2011).
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by $\theta$ frequency stimulation is regulated by a protein phosphate-operated gate." The Journal of Neuroscience, 2000, vol. 20, No. 21, pp. 7880-7887.
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cannon, et al.; "Endophenotypes in the Genetic Analyses of Mental Disorders"; Annu. Rev. Clin. Psychol.; vol. 2, pp. 267-290 (2006).
Cardin, et al. "Driving Fast spiking Cells Induces Gamma Rhythm and Controls Sensory Responses", 2009, Nature, vol. 459, vol. 7247, pp. 663-667.
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Cazillis, et al., "VIP and PACAP induce selective neuronal differentiation of mouse embryonic stem cells", Eur J Neurosci, 2004, 19(4):798-808.
Cenatiempo "Prokaryotic gene expression in vitro: transcription-translation coupled systems", Biochimie, 1986, vol. 68(4): pp. 505-515.
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Chow, et al.; "High-performance genetically targetable optical neural silencing by light-driven proton pumps"; Nature; vol. 463, pp. 98-102 (Jan. 7, 2010).
Chow et al., "Optogenetics and translation medicine", Sci Transl Med., 2013, 5(177):177.

(56) References Cited

OTHER PUBLICATIONS

Clark, et al.; "A future for transgenic livestock"; Nature Reviews Genetics; vol. 4, No. 10, pp. 825-833 (Oct. 2003).
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Crouse, et al. "Expression and amplification of engineered mouse dihydrofolate reductase minigenes" Mol. Cell. Biol. , 1983, vol. 3(2): pp. 257-266.
Cucchiaro et al., "Electron-Microscopic Analysis of Synaptic Input from the Perigeniculate Nucleus to A-Laminae of the Lateral Geniculate Nucleus in Cats", The Journal of Comparitive Neurology, 1991, vol. 310, pp. 316-336.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cui, et al., "Electrochemical deposition and characterization of conducting polymer polypyrrole/PSS on multichannel neural probes," Sensors and Actuators, 2001, vol. 93(1): pp. 8-18.
Dalva, et al. "Rearrangements of Synaptic Connections in Visual Cortex Revealed by Laser Photostimulation", Science, 1994,vol. 265, pp. 255-258.
Date, et al. "Grafting of Encapsulated Dopamine-Secreting Cells in Parkinson's Disease: Long-Term Primate Study", Cell Transplant, 2000, vol. 9, pp. 705-709.
Davidson, et al.; "Viral Vectors for Gene Delivery to the Nervous System"; Nature Reviews Neuroscience; vol. 4, pp. 353-364 (May 2003).
Davis; "The many faces of epidermal growth factor repeats," The New Biologist; vol. 2, No. 5, pp. 410-419 (1990).
Day, et al.; "The Nucleus Accumbens and Pavlovian Reward Learning"; Neuroscientist; vol. 13, No. 2, pp. 148-159 (Apr. 2007).
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
Dederen, et al. "Retrograde neuronal tracing with cholera toxin B subunit: comparison of three different visualization methods", Histochemical Journal, 1994, vol. 26, pp. 856-862.
Definition of Implant; Merriam-Webster Dictionary; retrieved Nov. 7, 2016 (http://www.merriam-webster.com/dictionary/implant).
Definition of Psychosis (2015).
Deisseroth "Next-generation optical technologies for illuminating genetically targeted brain circuits," The Journal of Neuroscience, 2006, vol. 26, No. 41, pp. 10380-10386.
Deisseroth et al., "Excitation-neurogenesis Coupling in Adult Neural Stem/Progenitor Cells", 2004, Neuron, vol. 42, pp. 535-552.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Signaling from Synapse to Nucleus: the logic Behind the Mechanisms", Currrent Opinion in Neurobiology, 2003, vol. 13, pp. 354-365.
Deisseroth et al., "Translocation of Calmodulin to the Nucleus Supports CREB Phosphorylation in Hippocampal Neurons", Nature, 1998, vol. 392, pp. 198-202.
Deisseroth, et al. "Controlling the Brain with Light", Scientific American, 2010, vol. 303, pp. 48-55.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Denk, W., et al. "Anatomical and functional imaging of neurons using 2-photon laser scanning microscopy", Journal of Neuroscience Methods, 1994, vol. 54, pp. 151-162.
Deonarain; "Ligand-targeted receptor-mediated vectors for gene delivery"; Exp. Opin. Ther. Patents; vol. 8, No. 1, pp. 53-69 (1998).
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.
Do Carmo, et al.; "Modeling Alzheimer's disease in transgenic rats"; Molecular Neurodegeneration; vol. 8, No. 37, 11 pages (2013).
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Ebert et al., "A Moloney MLV-rat somatotropin fusion gene produces biologically active somatotropin in a transgenic pig", Mol. Endocrinology, 1988, vol. 2, pp. 277-283.
EBI accession No. EMBL: J05199; "*N. pharaonis halorhodopsin* (hop) gene, complete cds"; (Nov. 22, 1990).
EBI accession No. UNIPROT: A7U0Y6; "SubName: Full=Bacteriorhodopsin"; (Aug. 10, 2010).
EBI accession No. UNIPROT: B0R5N9; "Subname: Full=Bacteriorhodopsin"; (Apr. 8, 2008).
EBI accession No. UNIPROT: B4Y103; "SubName: Full=Channelrhodopsin-1"; (Sep. 23, 2008).
EBI accession No. UNIPROT: P15647; "RecName: Full=Halorhodopsin; Short=HR; Alt Name: Full=NpHR"; (Apr. 1, 1990).
Edelstein, et al.; "Gene therapy clinical trials worldwide 1989-2004—an overview"; The Journal of Gene Medicine; vol. 6, pp. 597-602 (2004).
Ehrlich I. et al. "Amygdala inhibitory circuits and the control of fear memory", Neuron, 2009, vol. 62: pp. 757-771.
Eijkelkamp, et al. "Neurological perspectives on voltage-gated sodium channels", Brain, 2012, 135:2585-2612.
Eisen, "Treatment of amyotrophic lateral sclerosis", Drugs Aging, 1999; vol. 14, No. 3, pp. 173-196.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Ernst, et al. "Photoactivation of Channelrhodopsin", J. Biol. Chem., 2008, vol. 283, No. 3, pp. 1637-1643.
Esposito et al. "The integrase family of tyrosine recombinases: evolution of a conserved active site domain", Nucleic Acids Research, 1997, vol. 25, No. 18, pp. 3605-3614.
Evanko "Optical excitation yin and yang" Nature Methods, 2007, 4:384.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Fanselow, et al.; "Why We Think Plasticity Underlying Pavlovian Fear Conditioning Occurs in the Basolateral Amygdala"; Neuron; vol. 23, pp. 229-232 (Jun. 1999).
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fenno et al., "The development and application of optogenetics", Annual Review of Neuroscience, 2011, vol. 34, No. 1, pp. 389-412.

(56) References Cited

OTHER PUBLICATIONS

Ferenczi, et al.; "Optogenetic approaches addressing extracellular modulation of neural excitability"; Scientific Reports; vol. 6, 20 pages (Apr. 5, 2016).
Fiala et al., "Optogenetic approaches in neuroscience", Current Biology, Oct. 2010, 20(20):R897-R903.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Fox et al., "A gene neuron expression fingerprint of C. elegans embryonic motor neurons", BMC Genomics, 2005, 6(42):1-23.
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
Garrido et al., "A targeting motif involved in sodium channel clustering at the axonal initial segment", Science, 2003, vol. 300, No. 5628, pp. 2091-2094.
Gelvich et al. "Contact flexible microstrip applicators (CFMA) in a range from microwaves up to short waves," IEEE Transactions on Biomedical Engineering, 2002, vol. 49, Issue 9: 1015-1023.
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
GenBank Accession No. AC096118.6; Rattus norvegicus clone CH230-11 B15, 1-4, 24-25, Working Draft Sequence, 3 unordered pieces. May 10, 2003.
Genbank Accession No. BAA09452.1; Mukohata et al.; pp. 1 (Feb. 10, 1999).
Genbank Accession No. DQ094781 (Jan. 15, 2008).
GenBank Accession No. U79717.1; Rattus norvegicus dopamine 02 receptor 1-4, 24-25 gene, promoter region and exon 1. Jan. 31, 1997.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from Bacillus subtilis DNA" Gene, 1984, vol. 32(1-2): pp. 11-20.
Glick et al."Factors affecting the expression of foreign proteins in Escherichia coli", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gong, et al.; "Enhanced Archaerhodopsin Fluorescent Protein Voltage Indicators"; PLOS One; vol. 8, Issue 6, 10 pages (Jun. 2013).
Gonzalez, et al., "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.
Gorelova et al. , "The course of neural projection from the prefrontal cortex to the nucleus accumbens in the rat", Neuroscience, 1997, vol. 76, No. 3, pp. 689-706.
Goshen et al. "Dynamics of Retrieval Strategies for Remote Memories", Cell, 2011, col. 147: pp. 678-589.
Gottesman et al."Bacterial regulation: global regulatory networks," Ann. Rev. Genet. , 1984, vol. 18, pp. 415-441.
Gradinaru et al., "Optical Deconstruction of Parkinsonian neural circuitry," Science, Apr. 2009, 324(5925):354-359.
Gradinaru et al., "Targeting and readout strategies for fast optical neural control in vitro and in vivo", J Neuroscience, 2007, 27(52):14231-14238.
Gradinaru, et al. "ENpHR: a Natronomonas Halorhodopsin Enhanced for Optogenetic Applications", 2008, Brain Cell Biol., vol. 36 (1-4), pp. 129-139.
Gradinaru, et al., "Molecular and Cellular Approaches for Diversifying and Extending Optogenetics", Cell, 2010, vol. 141, No. 1, pp. 154-165.
Grady, et al.; "Age-Related Reductions in Human Recognition Memory Due to Impaired Encoding"; Science; vol. 269, No. 5221, pp. 218-221 (Jul. 14, 1995).
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for Streptomyces phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gunaydin et al., "Ultrafast optogenetic control", Nature Neuroscience, 2010, vol. 13, No. 3, pp. 387-392.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Haim, et al.; "Gene Therapy to the Nervous System"; Stem Cell and Gene-Based Therapy; Section 2, pp. 133-154 (2006).
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation in Vivo of a cloned mammalian gene: cadmium induces the transcription of a mouse metallothionein gene in SV40 vectors," Journal of Molecular Applied Genetics, 1982, vol. 1, No. 4, pp. 273-288.
Hammer et al., "Spontaneous inflammatory disease in transgenic rats expressing HLA-B27 and Human $β_2$m: an animal model of HLA-B27-associated human disorders", Cell, 1990, vol. 63, pp. 1099-1112.
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Han, et a.; "Virogenetic and optogenetic mechanisms to define potential therapeutic targets in psychiatric disorders"; Neuropharmacology; vol. 62, pp. 89-100 (2012).
Han, et al., "Millisecond-Timescale Optical Control of Neural Dynamics in the Nonhuman Primate Brain"; Neuron; vol. 62, pp. 191-198 (Apr. 30, 2009).
Han, et al., "Multiple-Color Optical Activation, Silencing, and Desynchronization of Neural Activity with Single-Spike Temporal Resolution", PLoS One, 2007, vol. 2, No. 3, pp. 1-12.
Han; et al., "Two-color, bi-directional optical voltage control of genetically-targeted neurons", CoSyne Abstract Presentation, Presented Feb. 24, 2007.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in Chlamydomonas rhodopsin", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.

(56) References Cited

OTHER PUBLICATIONS

Heymann, et al.; "Expression of Bacteriorhodopsin in Sf9 and COS-1 Cells"; Journal of Bioenergetics and Biomembranes; vol. 29, No. 1, pp. 55-59 (1997).
Hikida et al., "Acetlycholine enhancement in the nucleus accumbens prevents addictive behaviors of cocaine and morphine", PNAS, May 2003, 100(10):6169-6173.
Hikida et al., "Increased sensitivity to cocaine by cholingergic cell ablation in nucleus accumbens," PNAS, Nov. 2001, 98(23):13351-13354.
Hildebrandt et al, "Bacteriorhodopsin expressed in *Schizosaccharomyces pombe* pumps protons through the plasma membrane," PNAS, 1993, vol. 90, pp. 3578-3582.
Hira et al., "Transcranial optogenetic stimulation for functional mapping of the motor cortex", J Neurosci Methods, 2009, vol. 179, pp. 258-263.
Hirase, et al. "Multiphoton stimulation of neurons", J Neurobiol, 2002, vol. 51, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hofherr et al. "Selective Golgi export of Kir2.1 controls the stoichiometry of functional Kir2.x channel heteromers" Journal of Cell Science, 2005, vol. 118, p. 1935-1943.
Hosokawa, T. et al. "Imaging spatio-temporal patterns of long-term potentiation in mouse hippocampus." Philos. Trans. R. Soc. Lond. B., 2003, vol. 358, pp. 689-693.
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Hustler; et al., "Acetylcholinesterase staining in human auditory and language cortices: regional variation of structural features", Cereb Cortex (Mar.-Apr. 1996), 6(2):260-70.
Hynynen, et al. "Clinical applications of focused ultrasound—The brain." Int. J. Hyperthermia, 2007, vol. 23, No. 2: pp. 193-202.
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
International Search Report for International Application No. PCT/US2009/053474, dated Oct. 8, 2009.
Isenberg et al., "Cloning of a Putative Neuronal Nicotinic Aceylcholine Receptor Subunit"; Journal of Neurochemistry; vol. 52, No. 3, pp. 988-991 (1989).
Iyer et al., "Virally mediated optogenetic excitation and inhibition of pain in freely moving nontransgenic mice", Nat Biotechnol., 2014, 32(3):274-8.
Jekely, "Evolution of Phototaxis", 2009, Phil. Trans. R. Soc. B, vol. 364, pp. 2795-2808.
Jennings et al., "Distinct extended amygdala circuits for divergent motivational states," Nature, 2013, 496:224-228.
Ji et al., "Light-evoked Somatosensory Perception of Transgenic Rats that Express Channelrhodopsin-2 in Dorsal Root Ganglion Cells", PLoS One, 2012 7(3):e32699.
Jimenez S.A & Maren S. et al/ "Nuclear disconnection within the amygdala reveals a direct pathway to fear", Learning Memory, 2009, vol. 16: pp. 766-768.
Johansen, et al., "Optical Activation of Lateral Amygdala Pyramidal Cells Instructs Associative Fear Learning", 2010, PNAS, vol. 107, No. 28, pp. 12692-12697.
Johnson, et al.; "Differential Biodistribution of Adenoviral Vector in Vivo as Monitored by Bioluminescence Imaging and Quantitative Polymerase Chain Reaction"; Human Gene Therapy; vol. 17, pp. 1262-1269 (Dec. 2006).

Johnson-Saliba, et al.; "Gene Therapy: Optimising DNA Delivery to the Nucleus"; Current Drug Targets; vol. 2, pp. 371-399 (2001).
Johnston et al. "Isolation of the yeast regulatory gene GAL4 and analysis of its dosage effects on the galactose/melibiose regulon," PNAS, 1982, vol. 79, pp. 6971-6975.
Jones, et al.; "Animal Models of Schizophrenia"; British Journal of Pharmacology; vol. 164, pp. 1162-1194 (2011).
Kaiser; "Clinical research. Death prompts a review of gene therapy vector"; Science; 317(5838):580, 1 page (Aug. 3, 2007).
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: II. After-Potentials and Repetitive Firing", J Neurophysiol., 1961, vol. 24, pp. 243-259.
Karra, et al. "Transfection Techniques for Neuronal Cells", The Journal of Neuroscience, 2010, vol. 30, No. 18, pp. 6171-6177.
Karreman et al. "On the use of double FLP recognition targets (FRTs) in the LTR of retroviruses for the construction of high producer cell lines", Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Kay; "State-of-the-art gene-based therapies: the road ahead"; Nature Reviews Genetics; vol. 12, pp. 316-328 (May 2011).
Kelder et al., "Glycoconjugates in human and transgenic animal milk", Advances in Exp. Med. and Biol., 2001, vol. 501, pp. 269-278.
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khosravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Kim et al., "Diverging neural pathways assemble a behavioural state from separable features in anxiety" Nature, 2013, 496(7444):219-23.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kim et al., "PDZ domain proteins of synapses", Nature Reviews Neuroscience, 2004, vol. 5, No. 10, pp. 771-781.
Kingston et al. "Transfection and Expression of Cloned DNA," Supplement 31, Current Protocols in Immunology, 1999, 10.13.1-1 0.13.9.
Kingston et al. "Transfection of DNA into Eukaryotic Cells," Supplement 63, Current Protocols in Molecular Biology, 1996, 9.1.1-9.1.11, 11 pages.
Kinoshita, et al., "Optogenetically Induced Supression of Neural Activity in the Macaque Motor Cortex", Poster Sessions Somatomotor System, Others, Society for Neuroscience Meeting, 2010, pp. 141-154.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitabatake et al., "Impairment of reward-related learning by cholinergic cell ablationn in the striatum", PNAS, Jun. 2003, 100(13):7965-7970.
Kitayama, et al. "Regulation of neuronal differentiation by N-methyl-D-aspartate receptors expressed in neural progenitor cells

(56) References Cited

OTHER PUBLICATIONS isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Knopfel, et al. "Optical Probing of Neuronal Circuit Dynamics: Gentically Encoded Versus Classical Fluorescent Sensors", 2006, Trends Neurosci, vol. 29, No. 3, pp. 160-166.
Knopfel, et al.; "A comprehensive concept of optogenetics"; Progress in Brain Research; vol. 196, pp. 1-28 (2012).
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Kokel et al., "Photochemical activation of TRPA1 channels in neurons and animals", Nat Chem Biol, 2013, 9(4):257-263.
Kuhlman et al. (2008) "High-Resolution Labeling and Functional Manipulation of Specific Neuron Types in Mouse Brain by Cre-Activated Viral Gene Expression" PLoS One, e2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Lalumiere, R., "A new technique for controlling the brain: optogenetics and its potential for use in research and the clinic", Brain Stimulation, 2011, vol. 4, pp. 1-6.
Lammel et al., "Input-specific control of reward and aversion in the ventral tegmental area", Nature, 2012, 491(7423): 212-217.
Landy, A. "Mechanistic and structural complexity in the site-specific recombination pathways of Int and FLP", Current Opinion in Genetics and Development, 1993, vol. 3, pp. 699-707.
Lanyi et al. "The primary structure of a Halorhodopsin from Natronobacterium Pharaonis" Journal of Biological Chemistry, 1990, vol. 265, No. 3, p. 1253-1260.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gene Therapy Can Prevent Neuron Death Resulting from Necrotic and Apoptotic Insults", Journal of Neurochemistry, 2003, vol. 85: pp. 1079-1088.
Levitan et al. "Surface Expression of Kv1 Voltage-Gated K+ Channels is Governed by a C-terminal Motif," Trends Cardiovasc. Med., 2000, vol. 10, No. 7, pp. 317-320.
Li, et al.; "A Method for Activation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Li et al. "Fast noninvasive activation and inhibition of neural and network activity by vertebrate rhodopsin and green algae channelrhodopsin." PNAS, 2005, vol. 102, No. 49, p. 17816-17821.
Li et al., "Surface Expression of Kv1 Channels is Governed by a C-Terminal Motif", J. Biol. Chem. (2000), 275(16):11597-11602.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992,vol. 9, pp. 861-871.
Lin, "A user's guide to channelrhodopsin variants: features, limitations and future developments", Exp Physiol, 2010, vol. 96, No. 1, pp. 19-25.
Liske et al., "Optical inhibition of motor nerve and muscle activity in vivo", Muscle Nerve, 2013, 47(6):916-21.
Liu et al., "Optogenetics 3.0", Cell, Apr. 2010, 141(1):22-24.

Llewellyn et al., "Orderly recruitment of motor units under optical control in vivo", Nat Med., 2010, 16(10):1161-5.
Loetterle, et al., "Cerebellar Stimulation: Pacing the Brain", American Journal of Nursing, 1975, vol. 75, No. 6, pp. 958-960.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of FRT sites in the maize genome," Nucleic Acids Research , 1996, vol. 24, No. 19: pp. 3784-3789.
Ma et al. "Role of ER Export Signals in Controlling Surface Potassium Channel Numbers," Science, 2001, vol. 291, pp. 316-319.
Malin et al., "Involvement of the rostral anterior cingulate cortex in consolidation of inhibitory avoidance memory: Interaction with the basolateral amygdala", Neurobiol Learn Mem., Feb. 2007, 87(2):295-302.
Mancuso et al., "Optogenetic probing of functional brain circuitry", Experimental Physiology, 2010, vol. 96.1, pp. 26-33.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mann; "Synapses"; The Nervous System in Action; Chapter 13, http://michaeldmann.net/mann13.html (downloaded Apr. 2014).
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Mattis et al., "Principles for applying optogenetic tools derived from direct comparative analysis of microbial opsins", Nat Methods, 2011, 9(2):159-72.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
Mayford et al., "Control of memory formation through regulated expression of CaMKII transgene", Science, Dec. 1996, 274(5293):1678-1683.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging , 2001, vol. 24, No. 3, pp. 366-372.
Milella et al. "Opposite roles of dopamine and orexin in quinpirole-induced excessive drinking: a rat model of psychotic polydipsia" Psychopharmacology, 2010, 211:355-366.
Monje et al., "Irradiation Induces Neural Precursor-Cell Dysfunction", Natural Medicine, 2002, vol. 8, No. 9, pp. 955-962.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Mortensen et al. "Selection of Transfected Mammalian Cells," Supplement 86, Current Protocols in Molecular Biology, 1997, 9.5.1-09.5.19.

(56) References Cited

OTHER PUBLICATIONS

Mourot et al., "Rapid Optical Control of Nociception with an Ion Channel Photoswitch", Nat Methods, 2012, 9(4):396-402.
Mueller, et al.; "Clinical Gene Therapy Using Recombinant Adeno-Associated Virus Vectors"; Gene Therapy; vol. 15, pp. 858-863 (2008).
Mullins et al., "Expression of the DBA/2J Ren-2 gene in the adrenal gland of transgenic mice", EMBO, 1989, vol. 8, pp. 4065-4072.
Mullins et al., "Fulminant hypertension in transgenic rats harbouring the mouse Ren-2 gene", Nature, 1990, vol. 344, pp. 541-544.
Nacher, et al. "NMDA receptor antagonist treatment increases the production of new neurons in the aged rat hippocampus", Neurobiology of Aging, 2003,vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using *Drosophila* Rh1-bovine rhodopsin chimeras," Vision Res., 2006, vol. 46, No. 27: pp. 4575-4581.
Nieh et al., "Optogenetic dissection of neural circuits underlying emotional valence and motivated behaviors", Brain Research, E-pub 2012, 1511:73-92.
Nirenberg, et al. "The Light Response of Retinal Ganglion Cells is Truncated by a Displaced Amacrine Circuit", Neuron, 1997, vol. 18: pp. 637-650.
No Authors Listed; "Two bright new faces in gene therapy," Nature Biotechnology, 1996, vol. 14: p. 556.
Nonet, "Visualization of synaptic specializations in live C. elegans with synaptic vesicle protein-GFP fusions", J. Neurosci. Methods, 1999, 89:33-40.
Nunes-Duby, et al. "Similarities and differences among 105 members of the Int family of site-specific recombinases", Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Packer, et al.; "Targeting Neurons and Photons for Optogenetics"; Nature Neuroscience; vol. 16, No. 7, pp. 805-815 (Jul. 2013).
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Palmer et al., "The Adult Rat Hippocampus Contains Primordial Neural Stem Cells", Molecular and Cellular Neuroscience, 1997, vol. 8, pp. 389-404.
Palu, et al.; "In pursuit of new developments for gene therapy of human diseases"; Journal of Biotechnology; vol. 68, pp. 1-13 (1999).
Pan et al. "Functional Expression of a Directly Light-Gated Membrane Channel in Mammalian Retinal Neurons: A Potential Strategy for Restoring Light Sensitivity to the Retina After Photoreceptor Degeneration"; Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.

Pandya, et al.; "Where in the Brain Is Depression?"; Curr. Psychiatry Rep.; vol. 14, pp. 634-642 (2012).
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 .1-9.1 1 .1 8.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Peterlin, et al. "Optical probing of neuronal circuits with calcium indicators," PNAS, 2000, vol. 97, No. 7: pp. 3619-3624.
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Petersen et al. "Spatiotemporal Dynamics of Sensory Responses in Layer 2/3 of Rat Barrel Cortex Measured in Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Pfeifer, et al.; "Gene Therapy: Promises and Problems"; Annu. Rev. Genomics Hum. Genet.; vol. 2, pp. 177-211 (2001).
Pinkham et al., "Neural bases for impaired social cognition in schizophrenia and autism spectrum disorders", Schizophrenia Research, 2008, vol. 99, pp. 164-175.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Powell, et al.; "Schizophrenia-Relevant Behavioral Testing in Rodent Models: A Uniquely Human Disorder?"; Biol. Psychiatry; vol. 59, pp. 1198-1207 (2006).
Qiu et al. "Induction of photosensitivity by heterologous expression of melanopsin", Nature, 2005, vol. 433: pp. 745-749.
Ramalho, et al.; "Mouse genetic corneal disease resulting from transgenic insertional mutagenesis"; Br. J. Ophthalmol.; vol. 88, No. 3, pp. 428-432 (Mar. 2004).
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Rathnasingham et al., "Characterization of implantable microfabricated fluid delivery devices," IEEE Transactions on Biomedical Engineering, 2004, vol. 51, No. 1: pp. 138-145.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Ristevski; "Making Better Transgenic Models: Conditional, Temporal, and Spatial Approaches"; Molecular Biotechnology; vol. 29, No. 2, pp. 153-163 (Feb. 2005).

(56) References Cited

OTHER PUBLICATIONS

Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.
Rogers, et al.; "Effects of ventral and dorsal CA1 subregional lesions on trace fear conditioning"; Neurobiology of Learning and Memory; vol. 86, pp. 72-81 (2006).
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Sajdyk, et al., "Excitatory Amino Acid Receptors in the Basolateral Amygdala Regulate Anxiety Responses in the Social Interaction Test", Brain Research, 1997, vol. 764, pp. 262-264.
Salzman, et al. "Cortical microstimulation influences perceptual judgements of motion direction", Nature, 1990, vol. 346, pp. 174-177.
Samuelson; "Post-traumatic stress disorder and declarative memory functioning: a review"; Dialogues in Clinical Neuroscience; vol. 13, No. 3, pp. 346-351 (2011).
Santana et al., "Can Zebrafish Be Used as Animal Model to Study Alzheimer's Disease?" Am. J. Neurodegener. Dis. (2012), 1(1):32-48.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depression," Neuropsychopharmacology, 2008, vol. 33, pp. 368-377.
Schroll et al., "Light-induced activation of distinct modulatory neurons triggers appetitive or aversive learning in *Drosophila larvae*", Current Biology, Sep. 2006, 16(17):1741-1747.
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Sclimenti, et al. "Directed evolution of a recombinase for improved genomic integration at a native human sequence," Nucleic Acids Research, 2001, vol. 29, No. 24: pp. 5044-5051.
Sheikh et al., "Neurodegenerative Diseases: Multifactorial Conformational Diseases and Their Therapeutic Interventions", Journal of Neurodegenerative Diseases (2013), Article ID 563481:1-8.
Shepherd, et al. "Circuit Analysis of Experience-Dependent Plasticity in the Developing Rat Barrel Cortex", Neuron, 2003, vol. 38: pp. 277-289.
Shibasaki et al. "Effects of body temperature on neural activity in the hippocampus: Regulation of resting membrane potentials by transient receptor potential vanilloid 4," The Journal of Neuroscience, 2007, 27(7):1566-1575.
Shimizu, et al.; "NMDA Receptor-Dependent Synaptic Reinforcement as a Crucial Process for Memory Consolidation"; Science; vol. 290, pp. 1170-1174 (Nov. 10, 2000).
Shoji, et al.; "Current Status of Delivery Systems to Improve Target Efficacy of Oligonucleotides"; Current Pharmaceutical Design; vol. 10, pp. 785-796 (2004).
Sigmund; "Viewpoint: Are Studies in Genetically Altered Mice Out of Control?"; Arterioscler Thromb Vasc Biol.; vol. 20, No, 6, pp. 1425-1429 (Jun. 2000).
Silver, et al. "Amino terminus of the yeast GAL4 gene product is sufficient for nuclear localization" PNAS, 1984, vol. 81, No. 19: pp. 5951-5955.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Sineshchekov et al., "Two Rhodopsins Mediate Phototaxis to Low and High Intensity Light in Chlamydomas Reinhardtil", PNAS, 2002, vol. 99, No. 13, pp. 8689-8694.
Sineshchekov et al.; "Intramolecular Proton Transfer in Channelrhodopsins"; Biophysical Journal; vol. 104, No. 4, pp. 807-817 (Feb. 2013).
Singer et al. "Elevated Intrasynaptic Dopamine Release in Tourette's Syndrome Measured by PET," American Journal of Psychiatry, 2002, vol. 159: pp. 1329-1336.
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Slamovits et al., "A bacterial proteorhodopsin proton pump in marie eukaryotes", Nature Comm, 2011, 2:183.
Slimko et al., "Selective Electrical Silencing of Mammalian Neurons in Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Sohal et al., "Parvalbumin neurons and gamma rhythms enhance cortical circuit performance", Nature, 2009, vol. 459, No. 7247, pp. 698-702.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Stonehouse, et al.; "Caffeine Regulates Neuronal Expression of the Dopamine 2 Receptor Gene"; Molecular Pharmacology; vol. 64, No. 6, pp. 1463-1473 (2003).
Suzuki et al., "Stable Transgene Expression from HSV Amplicon Vectors in the Brain: Potential Involvement of Immunoregulatory Signals", Molecular Therapy (2008), 16(10):1727-1736.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.

(56) References Cited

OTHER PUBLICATIONS

Takahashi, et al."Diversion of the Sign of Phototaxis in a *Chlamydomonas reinhardtii* Mutant Incorporated with Retinal and its Analogs," FEBS Letters, 1992, vol. 314, No. 3, pp. 275-279.
Takahashi, et al., "Induction of Pluripotent Stem Cells from Mouse Embryonic and Adult Fibroblast Cultures by Defined Factors", 2006, Cell, vol. 126, pp. 663-676.
Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.
Tamai, "Progress in Pathogenesis and Therapeutic Research in Retinitis Pigmentosa and Age Related Macular Degeneration", Nippon Ganka Gakkai Zasshi, Dec. 2004, 108(12):750-769.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Taurog et al., "HLA-B27 in inbred and non-inbred transgenic mice", J. Immunol., 1988, vol. 141, pp. 4020-4023.
Thomas et al., "Progress and Problems with the Use of Viral Vectors for Gene", Nat. Rev. Genet. (2003), 4(5):346-358.
Tønnesen, et al., "Optogenetic Control of Epileptiform Activity", PNAS, 2009, vol. 106, No. 29, pp. 12162-12167.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Towne et al., "Efficient transduction of non-human primate motor neurons after intramuscular delivery of recombinant AAV serotype 6", Gene Ther., 2010, 17(1):141-6.
Towne et al., "Optogenetic control of targeted peripheral axons in freely moving animals", PLoS One, 2013, 8(8):e72691.
Towne et al., "Recombinant adeno-associated virus serotype 6 (rAAV2/6)-mediated gene transfer to nociceptive neurons through different routes of delivery", Mol Pain, 2009, 5:52.
Tsai, et al., "Phasic Firing in Dopaminergic Neurons in Sufficient for Behavioral Conditioning", Science, 2009, vol. 324, pp. 1080-1084.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
Tye et. al., "Amygdala circuitry mediating reversible and bidirectional control of anxiety", Nature, 2011, vol. 471(7338): pp. 358-362.
Tye et. al., Supplementary Materials: "Amygdala circuitry mediating reversible and bidirectional control of anxiety,", Nature, 2011, vol. 471(7338): pp. 358-362.
Tye, et al. "Optogenetic investigation of neural circuits underlyding brain disease in animal models," Nature Reviews Neuroscience (Mar. 2012), 13(4):251-266.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Verma, et al.; "Gene therapy—promises, problems and prospects"; Nature; vol. 389, pp. 239-242 (Sep. 1997).
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.

Wagner, "Noninvasive Human Brain Stimulation", Annual Rev. Biomed. Eng. 2007. 9:I9.1-19.39.
Wall, "Transgenic livestock: Progress and prospects for the future", Theriogenology, 1996, vol. 45, pp. 57-68.
Wang, et al. "Direct-current Nanogenerator Driven by Ultrasonic Waves," Science, 2007, vol. 316, pp. 102-105.
Wang, et al., "High-speed mapping of synaptic connectivity using photostimulation in Channelrhodopsin-2 transgenic mice", PNAS, 2007, vol. 104, No. 19, pp. 8143-8148.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Wang, et al., "Mrgprd-Expressing Polymodal Nociceptive Neurons Innervate Most Known Classes of Substantia Gelatinosa Neurons", J Neurosci, 2009, 29(42):13202-13209.
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Wang, et al.; "Simultaneous phase and size control of upconversion nanocrystals through lanthanide doping"; Nature; vol. 463, No. 7284, pp. 1061-1065 (Feb. 25, 2010).
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Williams et al., "From optogenetic technologies to neuromodulation therapies", Sci Transl Med., 2013, 5(177):177.
Witten et. al., "Cholinergic Interneurons Control Local Circuit Activity and Cocaine Conditioning", Science, 2010, vol. 330, No. 6011: pp. 1677-1681.
Witten et. al., Supporting Online Material for: "Cholinergic Interneurons Control Local Circuit Activity and Cocaine Conditioning", Science, 2010, vol. 330:17 pages.
Written opinion of PCT Application No. PCT/US2011/059383 (dated May 9, 2012).
Xiong et al., "Interregional connectivity to primary motor cortex revealed using MRI resting state images", Hum Brain Mapp, 1999, 8(2-3):151-156.
Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.
Yizhar et al., "Optogenetics in neural systems", Neuron Primer, vol. 71, No. 1, pp. 9-34 (Jul. 14, 2011).
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.

(56) References Cited

OTHER PUBLICATIONS

Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Zhang "Multimodal fast optical interrogation of neural circuitry," Nature, 2007, vol. 446, pp. 633-641.
Zhang, et al. "Channelrhodopsin-2 and optical control of excitable cells," Nature Methods,2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008,vol. 11, No. 6, pp. 631-633.
Zhang, et al., "The Microbial Opsin Family of Optogenetic Tools", Cell, 2011, vol. 147, No. 7, pp. 1146-1457.
Zhang, et al.; "Optogenetic interrogation of neural circuits: Technology for probing mammalian brain structures"; Nature Protocols; vol. 5, No. 3, pp. 439-456 (Feb. 18, 2010).
Zhao, et al., "Improved Expression of Halorhodopsin for Light-Induced Silencing of Neuronal Activity", Brain Cell Biology, 2008, vol. 36 (1-4), pp. 141-154.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient in Vivo Gene Delivery", Journal of Virology, 1998, vol. 72, No. 12, pp. 9873-9880.
Azizgolshani, et al.; "Reconstituted plant viral capsids can release genes to mammalian cells"; Virology; vol. 441, No. 1, pp. 12-17 (2013).
Racaniello; "How many viruses on Earth?"; Virology Blog; 6 pages; http://www.virology.ws/2013/09/06/how-many-viruses-on-earth/ (Sep. 6, 2013).
Lin, et al.; "Study of the Circuitry of Nucleus Accumbens and its Effect on Addiction by Optogenetic Methods: 964"; Neurosurgery; vol. 67, No. 2, p. 557 (Aug. 2010).
Tsuchida; "Nervous Control of Micturition"; The Japanese Journal of Urology; vol. 80, No. 9, pp. 1257-1277 (1989).
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).
Sofuoglu, et al.; "Cholinergic Functioning in Stimulant Addiction: Implications for Medications Development"; CNS Drugs; vol. 23, No. 11, pp. 939-952 (Nov. 1, 2009).
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
Definition of integral. Merriam-Webster Dictionary, retrieved on Mar. 20, 2017; Retrieved from the Internet: <http://www.merriam-webster.com/dictionary/integral>.
Abbott, et al.; "Photostimulation of Retrotrapezoid Nucleus Phox2b-Expressing Neurons in Vivo Produces Long-Lasting Activation of Breathing in Rats"; The Journal of Neuroscience; vol. 29, No. 18, pp. 5806-5819 (May 6, 2009).
Alilain, et al.; "Light-Induced Rescue of Breathing after Spinal Cord Injury"; The Journal of Neuroscience; vol. 28, No. 46, pp. 11862-11870 (Nov. 12, 2008).
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Coleman, et al.; "Assessing Anxiety in Nonhuman Primates"; Ilar Journal; vol. 55, No. 2, pp. 333-346 (2014).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).
Luo, et al.; "Synthetic DNA delivery systems"; Nature Biotechnology; vol. 18, pp. 33-37 (Jan. 2000).
Maestripieri, et al.; "A modest proposal: displacement activities as an indicator of emotions in primates"; Anim. Behav.; vol. 44, pp. 967-979 (1992).
Nelson, et al.; "Non-Human Primates: Model Animals for Developmental Psychopathology"; Neuropsychopharmacology; vol. 34, No. 1, pp. 90-105 (Jan. 2009).
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.
Daniel, et al.; "Stress Modulation of Opposing Circuits in the Bed Nucleus of the Stria Terminalis"; Neuropsychopharmacology Reviews; vol. 41, pp. 103-125 (2016).
Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).
Knopfel, et al.; "Remote control of cells"; Nature Nanotechnology; vol. 5, pp. 560-561 (Aug. 2010).
Steimer; "The biology of fear- and anxiety-related behaviors"; Dialogues in Clinical Neuroscience; vol. 4, No. 3, pp. 231-249 (Sep. 2002).
Stuber; "Dissecting the neural circuitry of addiction and psychiatric disease with optogenetics"; Neuropsychopharmacology; vol. 35, No. 1, pp. 341-342 (2010).
Bibel, et al.; "Differentiation of mouse embryonic stem cells into a defined neuronal lineage"; Nature Neuroscience; vol. 7, No. 9, pp. 1033-1009 (Sep. 2004).
Gerits, et al.; "Optogenetically Induced Behavioral and Functional Network Changes in Primates"; Current Biology; vol. 22, pp. 1722-1726 (Sep. 25, 2012).
Han, et al.; "Optogenetics in the nonhuman primate"; Prog. Brain Res.; vol. 196, pp. 215-233 (2012).
Boyden, et al.; "A history of optogenetics: the development of tools for controlling brain circuits with light"; F1000 Biology Reports; vol. 3, No. 11, 12 pages (May 3, 2011).
Knox, et al.; "Heterologous Expression of *Limulus* Rhodopsin"; The Journal of Biological Chemistry; vol. 278, No. 42, pp. 40493-40502 (Oct. 17, 2003).
Lin, et al.; "Characterization of Engineered Channelrhodopsin Variants with Improved Properties and Kinetics"; Biophysical Journal; vol. 96, No. 5, pp. 1803-1814 (Mar. 2009).

\* cited by examiner

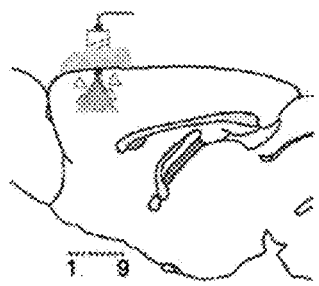
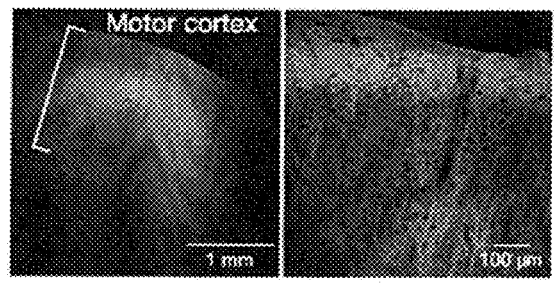
FIG. 5a  FIG. 5b
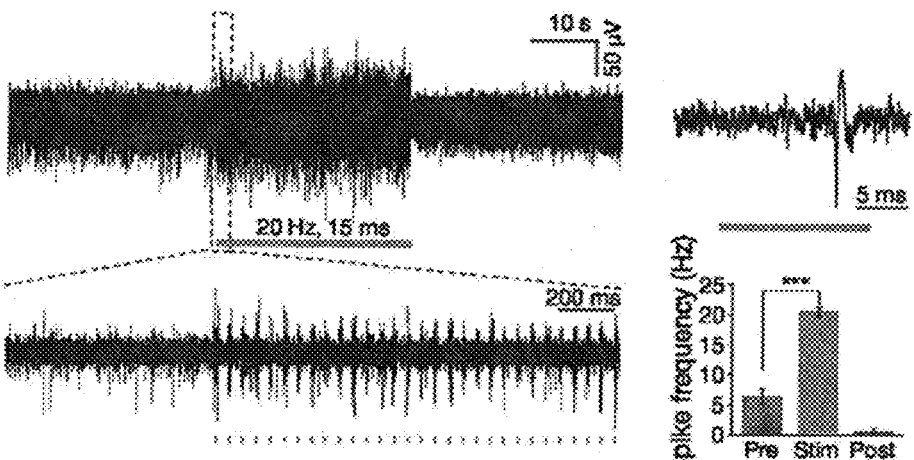
FIG. 5c
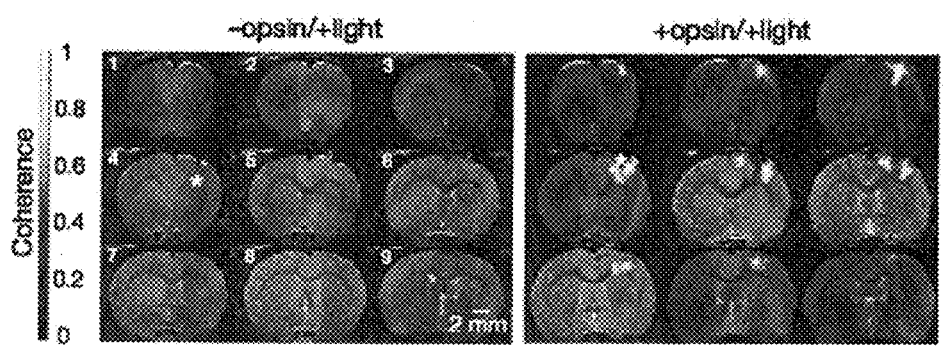
FIG. 5d

SEQUENCE LISTING

<160> NUMBER OF SEQ ID NOS: 2

<210> SEQ ID NO 1
<211> LENGTH: 310
<212> TYPE: PRT
<213> ORGANISM: Chlamydomonas reinhardtii

<400> SEQUENCE: 1

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala

```
            35                  40                  45
Gln Thr Ala Ser Asn Val Leu Gln Trp Leu Ala Ala Gly Phe Ser Ile
 50                  55                  60

Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                 85                  90                  95

Glu Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
        130                 135                 140

Tyr Ser Arg Arg Thr Met Gly Leu Leu Val Ser Asp Ile Gly Thr Ile
    145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 2
<211> LENGTH: 300
<212> TYPE: PRT
<213> ORGANISM: Volvox carteri

<400> SEQUENCE: 2

Met Asp Tyr Pro Val Ala Arg Ser Leu Ile Val Arg Tyr Pro Thr Asp
  1               5                  10                  15

Leu Gly Asn Gly Thr Val Cys Met Pro Arg Gly Gln Cys Tyr Cys Glu
                 20                  25                  30

Gly Trp Leu Arg Ser Arg Gly Thr Ser Ile Glu Lys Thr Ile Ala Ile
             35                  40                  45

Thr Leu Gln Trp Val Val Phe Ala Leu Ser Val Ala Cys Leu Gly Trp
 50                  55                  60

Tyr Ala Tyr Gln Ala Trp Arg Ala Thr Cys Gly Trp Glu Glu Val Tyr
 65                  70                  75                  80

Val Ala Leu Ile Glu Met Met Lys Ser Ile Ile Glu Ala Phe His Glu
                 85                  90                  95
```

-continued

```
Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
        115                 120                 125

His Leu Ser Asn Leu Thr Gly Leu Lys Asp Asp Tyr Ser Lys Arg Thr
        130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
        210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
            275                 280                 285

Met Glu Val Glu Thr Leu Val Ala Glu Glu Asp
        290                 295                 300
```

OPTOGENETIC MAGNETIC RESONANCE IMAGING

CROSS-REFERENCE TO RELATED APPLICATIONS

This application is a continuation of U.S. patent application Ser. No. 15/008,214, filed Jan. 27, 2016, now U.S. Pat. No. 9,615,789, which is a continuation of U.S. patent application Ser. No. 14/298,413, filed Jun. 6, 2014, now U.S. Pat. No. 9,271,674, which is a continuation of U.S. patent application Ser. No. 13/847,653, filed Mar. 20, 2013, now U.S. Pat. No. 8,834,546, which is a continuation of U.S. patent application Ser. No. 13/299,727, filed Nov. 18, 2011, now U.S. Pat. No. 8,696,722, which application claims benefit under 35 U.S.C. § 119 to U.S. Provisional Patent Application Ser. No. 61/416,143 filed on Nov. 22, 2010; U.S. patent application Ser. No. 15/008,214, U.S. patent application Ser. No. 14/298,413, U.S. patent application Ser. No. 13/847,653, U.S. patent application Ser. No. 13/299,727, and U.S. Patent Application No. 61/416,143 and its Appendix, including the references cited therein, are hereby incorporated by reference in their entirety.

FEDERALLY-SPONSORED RESEARCH AND DEVELOPMENT

This invention was made with government support under Contract Number EB008738 awarded by the National Institutes of Health. The government has certain rights in the invention.

BACKGROUND

Blood oxygenation level-dependent functional magnetic resonance imaging (BOLD fMRI) is a widely used technology for non-invasive whole brain imaging. BOLD signals reflect complex changes in cerebral blood flow (CBF), cerebral blood volume (CBV), and cerebral metabolic rate of oxygen consumption ($CMRO_2$) following neuronal activity. However, the neural circuits that trigger BOLD signals are not completely understood, which may confound fMRI interpretation. Candidate circuit elements for triggering various kinds of BOLD signals include excitatory neurons, mixed neuronal populations, astroglia, and axonal tracts or fibers of passage. Understanding the neural circuits that give rise to BOLD signals may provide a way to diagnose neurological disorders that impact specific circuits, as well as to screen for therapeutic agents to treat such disorders.

BRIEF SUMMARY OF THE INVENTION

The present disclosure is directed to apparatuses and methods involving the use of magnetic resonance imaging. Aspects of the disclosure include modifying a target neural cell population in a first region of a brain to express light-responsive molecules. Using a light pulse, the light-responsive molecules in the target neural cell population are stimulated. Multiple regions of the brain are scanned via magnetic resonance imaging. The scans allow for observation of a neural reaction in response to the stimulation in at least one of the multiple regions of the brain. In response to the observations, a determination is made whether neural projection in a second region of the brain are connected to at least some of the cells in the modified target cell population in the first region of the brain.

Aspects of the present disclosure relate generally to exciting and/or inhibiting neural cells in vivo using light and mapping of the neural response, by employing magnetic resonance imaging and methods relating to the optogenetic modification of cells. In a more specific embodiment, functional magnetic resonance imaging (fMRI) using blood oxygenation level-dependent (BOLD) signals is used to map neural responses.

Certain aspects of the present disclosure relate to integrating high-field fMRI output with optogenetic stimulation of cells. A light-activated, light-responsive molecule, for example an opsin, is introduced into specifically targeted cell types and circuit elements using cell type-specific promoters to allow millisecond scale targeted activity modulation in vivo. An opsin is light-activated and regulates the transmembrane conductance of a cell that expresses the opsin. The opsin can be a single component microbial light-activated conductance regulator. The genetic material of a desired opsin is modified to include cell type-specific promoters as well as promoters allowing for optimal expression in the animal. The opsin can be modified to express in mammalian cells, for example.

Other aspects of the present disclosure are directed to apparatuses and methods involving the modification of a target neural cell population in a first region of a brain to express light-responsive molecules. Following modification, the light-responsive molecules are stimulated in the target neural cell population by using a light pulse. While the target neural cell population is being stimulated, multiple regions of the brain are scanned using an fMRI machine. The fMRI scans are used to observe neural reaction in response to the stimulation in at least one of the multiple regions of the brain and to determine therefrom the network communication characteristics relating to, but is not necessarily the same as, the anatomical neural projection pattern.

Other aspects of the present disclosure are directed to apparatuses and methods involving verifying BOLD responses. The method includes modifying a target neural cell population to express light-responsive molecules in a first region of a brain. The light-responsive molecules excite the target cell population in response to light. The light-responsive molecules in the target neural cell population are stimulated using a light pulse. At least the first region of the brain is scanned with an fMRI machine during light stimulation of the target neural cell population. Based at least in part on a BOLD signal response in the target neural cell population due to light stimulation, a BOLD signal response is assessed from an electronic stimulation in the target neural cell population.

In some embodiments, modifying neural cells may comprise delivering a light-responsive molecule (e.g., ChR2) to neural cells of a first brain region. The neural cells of the first brain region may be stimulated by positioning an optical fiber at, and applying light pulses to, the first brain region. Multiple regions of the brain may be scanned by acquiring magnetic resonance images of first and second brain regions to identify the neural cells of the second brain region that are connected to the neural cells of the first brain region.

In other embodiments, the neural cells of the first brain region may be stimulated by positioning optical fiber at, and applying light pulses to, the second brain region. Multiple regions of the brain may be scanned by acquiring magnetic resonance images of first and second brain regions to identify the neural cells of the first brain region that are connected to the neural cells of the second brain region.

In some embodiments, the first brain region may be in the motor cortex and the second brain region may be in the thalamus, or vice versa. In other variations, the first brain region may be the anterior or the posterior thalamus. In some embodiments, the first brain region may be in the thalamus and the second brain region may be in the somatosensory cortex. Scanning multiple regions of the brain may comprise acquiring magnetic resonance images of bilateral regions of the somatosensory cortex and/or motor cortex.

Various embodiments, relating to and/or using such methodology and apparatuses, can be appreciated by the skilled artisan, particularly in view of the figures and/or the following discussion.

The above overview is not intended to describe each illustrated embodiment or every implementation of the present disclosure. While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims.

BRIEF DESCRIPTION OF THE DRAWINGS

Various example embodiments may be more completely understood in consideration of the following detailed description in connection with the accompanying drawings, in which:

FIG. 5 depicts one variation of a system and method for delivering a viral vector to a neuronal population for optogenetic stimulation and fMRI analysis. FIG. 5a shows transduced cell, represented by triangles, and the light and location (1 . . . 9) of coronal slices, indicated by dots. FIG. 5b shows confocal images of ChR2-EYFP expression in M1 (left); higher magnification (right). FIG. 5c shows optrode recordings during 473 nm optical stimulation (20 Hz/15 ms pulse width); spiking is significantly elevated (error bar indicates ±s.d., two-sample t-test; *** indicates P<0.001; n=3). "Pre" indicates spike frequency pre-stimulation; "Stim" indicates spike frequency during stimulation; "Post" indicates spike frequency post-stimulation. FIG. 5d shows BOLD activation observed with AAV5-CaMKIIα::ChR2-EYFP but not with saline injection (P<0.001; asterisk, optical stimulation).

FIG. 6 depicts nonlocal mapping of the casual role of cells defined by location and genetic identify, in accordance with an example embodiment of the present disclosure.

FIG. 7 depicts control of cells defined by location, genetic identity, and wiring during ofMRI, in accordance with an example embodiment of the present disclosure.

FIG. 8 shows recruitment of bilateral cortices by the anterior thalamus, in accordance with an example embodiment of the present disclosure.

DETAILED DESCRIPTION AND EXAMPLE EMBODIMENTS

Figure 1A:
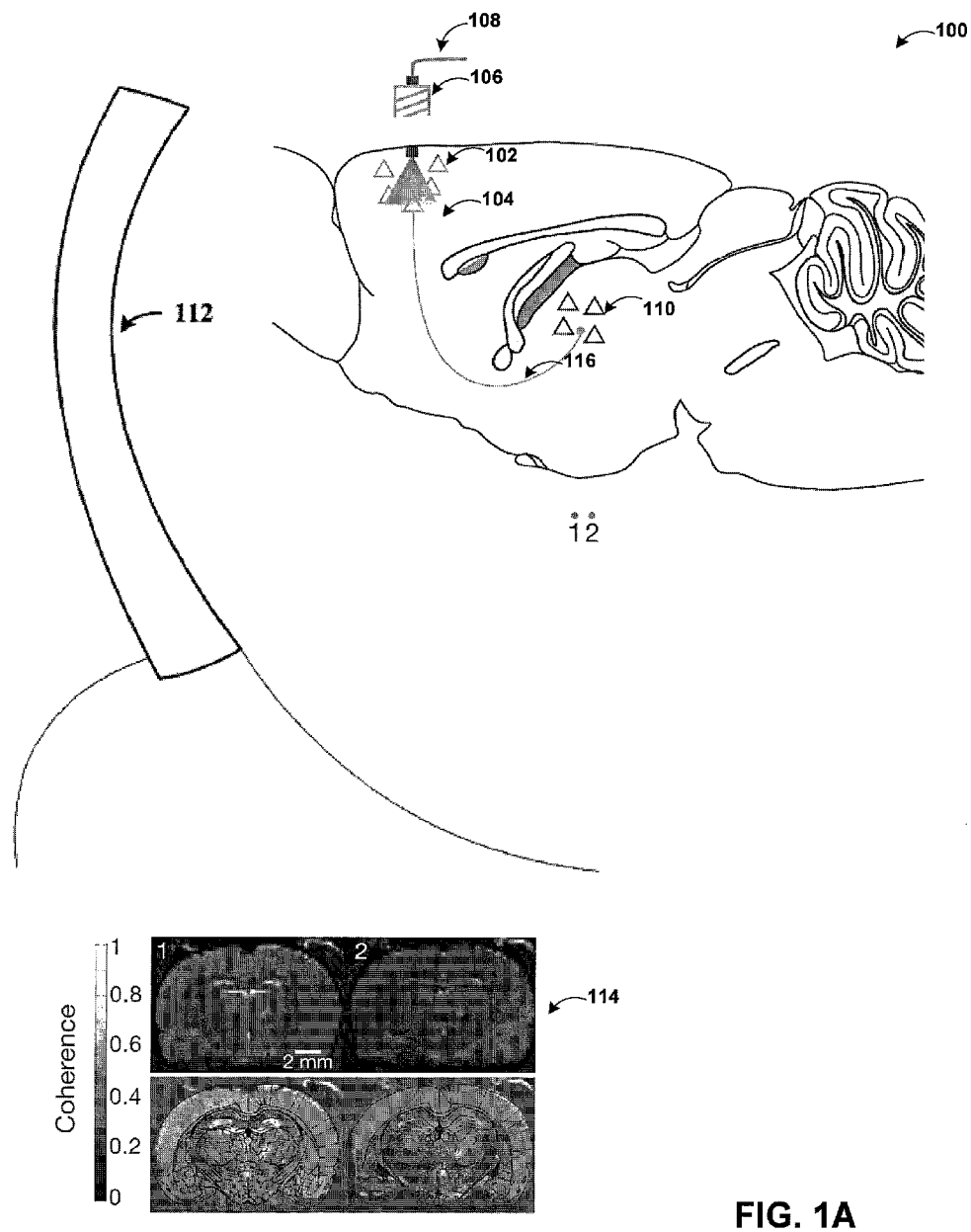
FIG. 1A shows a brain subjected to an optogenetic fMRI ("ofMRI"), in accordance with an example embodiment of the present disclosure.

Aspects of the present disclosure may be more completely understood in consideration of the detailed description of various embodiments of the present disclosure that follows in connection with the accompanying drawings. This description and the various embodiments are presented by way of the Examples and in "Global and local fMRI signals driven by neurons defined optogenetically by type and wiring," *Nature*, Vol. 465, 10 Jun. 2010, pp, 788-792, which is hereby incorporated by reference in its entirety. The embodiments and specific applications discussed herein may be implemented in connection with one or the above described aspects, embodiments and implementations, as well as those shown in the figures and described below. Reference may also be made to the following background publications: in U.S. Published Patent Application No. 2010/0190229, entitled "System for Optical Stimulation of Target Cells" to Zhang et al.; U.S. Published Patent Application No. 2010/0145418, also entitled "System for Optical Stimulation of Target Cells" to Zhang et al.; and U.S. Published Patent Application No. 2007/0261127, entitled "System for Optical Stimulation of Target Cells" to Boyden et al. These applications form part of the provisional patent document and are all hereby incorporated by reference in their entirety. As is apparent from these publications, numerous opsins can be used in mammalian cells in vivo and in vitro for provide optical stimulation and control of target cells. For example, when ChR2 is introduced into a cell, light activation of the ChR2 channelrhodopsin results in excitation and firing of the cell. In instances when NpHR is introduced into a cell, light activation of the NpHR opsin results in inhibition of the cell. These and other aspects of the disclosures of the above references patent applications may be useful in implementing various aspects of the present disclosure.

In certain embodiments of the present disclosure, a viral vector including a light sensitive molecule is injected in cells in the primary motor cortex of an animal. The viral vector infects a chosen cell type, for example cortical neurons, while not infecting surrounding cells of different cell types. A cannula is implanted into the animal's brain to allow access for both the injection of the virus and for an optical fiber to provide light to the infected cells. The cannula, optical fiber, and any other accessories are fabricated from magnetic resonance-compatible materials in order to minimize susceptibility artifact during MRI scanning. Light pulses are provided by the optical fiber to the cells that have been infected in the motor cortex. The wave length of the light is chosen based on the light-sensitive molecule introduced into the cell population. Light pulses are delivered to the neurons expressing the light-sensitive molecules. In response, an optically evoked BOLD signal is observed in the cortical grey matter at the virus injection and optical stimulation site. The BOLD signal is observed in fMRI slices of the motor cortex. Additional fMRI slices capture downstream responses during optical stimulation of the cortical neurons. The additional fMRI slices are centered on the thalamus, for example. The stimulation of the infected cells in the motor cortex results in cortico-thalamic axonal projection fibers being observed. A reaction is observed in the thalamus despite the fact that no cells in the thalamus have been infected with light sensitive molecules.

BOLD fMRI is a technology for non-invasive, whole-brain imaging. Bold signals reflect complex and incompletely understood changes in cerebral blood flow (CBF), Cerebral blood volume (CBV), and cerebral metabolic rate of oxygen consumption (CMRO2) following neuronal activity. For a variety of reasons, it is useful and important to understand what kinds of activity are capable of triggering BOLD responses.

In various embodiments of the present disclosure, the local stimulation of the cortex during fMRI is used to determine if unidirectionally triggered BOLD responses are being observed and measured. In this embodiment, antidromic drive found in electrical stimulation is eliminated, and allows for global causal connectivity mapping. Robust thalamic BOLD signals are observed in response to cortex stimulation. The properties of the thalamic response are distinct from the response in the cortex. For example, the thalamic response is delayed in time as compared to the response observed in the cortex.

In certain more specific embodiments, fMRI scanning occurs several days (e.g., in some instances, at least 10 days) after virus injection. fMRI signals are acquired in 0.5 mm coronal slices. To assess the neural response at the site of the injection, the slices are centered around the motor cortex. To assess the neural response at areas remote from the motor cortex 0.5 mm slices are acquired in the area of interest. A 473 nm light pulse is delivered by an optical fiber at a rate of 20 Hz, with a 15 ms pulse width to the targeted cells expressing the light-responsive molecules.

In another embodiment consistent with the present disclosure, a viral vector including a light sensitive molecule is injected in cells in the primary motor cortex of an animal. The viral vector delivers a light-responsive molecule to a chosen cell type, for example cortical neurons, while not infecting surrounding cells of different cell types. A cannula is implanted at a second location remote from the cortical neurons expressing the light-responsive molecule. The viral vector is injection into the motor cortex, and the cannula is implanted in the thalamus, for example. Providing light to the thalamus allows for confirmation of the functional projection patterns in the brain. The light-responsive molecules trigger spikes in illuminated photosensitive axons that both drive optical synaptic output and back-propagate through the axon to some of the stimulated cells. This permits optical fMRI mapping during selective control of the motor cortical cells that project to the thalamus. Robust BOLD signals are observed both locally in the thalamus and in the motor cortex. This result is consistent with the recruitment of the topologically targeted cells both locally and distally. It also demonstrates that stimulation of the axons of the neurons expressing the light-responsive molecules is sufficient to elicit BOLD responses in remote areas. This also illustrates the feasibility of in vivo mapping of the global impact of cells defined not only by anatomical location of the body of the cell and the genetic identity, but also the connection topology. The projections of the infected cells can be mapped based on the reaction of the axons to light stimulation at areas remote from the body of the cell.

In certain embodiments consistent with the present disclosure, a viral vector carrying a light-responsive molecule is injected into cells in the thalamus. A cannula is implanted in order to deliver light to the target cell population expressing the light-responsive molecules in the thalamus. Light is delivered to the target cells. fMRI scans of the thalamus as well as other areas of the brain allow functional mapping of the thalamic projections to the motor cortex. Scanning other regions of the brain as well can show responses in the sensory cortex or other parts of the brain as well. Because motor control and planning involve bilateral coordination, mapping of thalamic projections is more likely to involve both ipsilateral and contralateral pathways. The use of light stimulation of thalamic nuclei allows isolation of functional mapping of thalamocortical projections without also showing cortical-thalamic projections.

In certain more specific embodiments, it is shown that optical stimulation of posterior thalamic nuclei resulted in a strong BOLD response, both at the site of stimulation and in the posterior ipsilateral somatosensory cortex. Optically stimulating excitory cell bodies and fibers in anterior thalamic nuclei resulted in BOLD response at the site of stimulation and also ipsilateral and contralateral cortical BOLD responses consistent with the bilaterality of anterior thalamocortical nuclei involvement in motor control and coordination.

Turning to FIG. 1A, a section of a brain 100 is depicted. The brain 100 includes two regions, separated from each other, with cell populations of interest. The first target cell population 102 is modified to include a light-responsive molecule. The second cell population 110 is connected to the first target cell population 102 through a neural projection 116. An fMRI compatible cannula 106 is implanted and an optical fiber 108 is delivered through the cannula 106 to the target cell population 102. The optical fiber 108 provides light 104 to the light-responsive molecules in the target cell population 102. In response to the light delivery, the light-responsive molecules in the target cell population 102 are excited and the excitation spreads down the neural projection 116 to the cell population 110 in a second region of the brain. The progress of the excitation of the target cell population 102 and the remote cell population 110 is captured using an fMRI machine 112. The fMRI machine scans the brain 100 at designated areas. The results 114 of the fMRI scan show evidence of excitation in the remote cell population 110.

In certain embodiments the target cell population 102 is injected with a virus at the same cite as the cannula. The virus injection includes a viral vector virus to deliver a light-responsive molecule, such as channelrhodopsin (ChR2) to the target cell population. The viral vector includes promoters to drive expression of the ChR2 in the target cell population. The promoters can be chosen based on the target cell population 102 so that expression of ChR2 is limited to the desired cell type. For example, in adult rats an adeno-associated viral vector AAV5-CaMKIIα::ChR2 (H134R)-EYFP can be used to drive expression of a ChR2 specifically in $Ca^{2+}$/calmodulin-dependent protein kinase IIα (CaMKIIα)-expressing principal cortical neurons, but not in neighboring GABAergic or glial cells. In embodiments where ChR2 is the light-responsive molecule, the optical fiber 108 provides a 473 nm light pulse at 20 Hz. This has been found to reliably drive local neuronal firing in vivo.

In more particular embodiments viral injection occurred at least 10 days before the fMRI scans were taken.

In certain embodiments the target cell population 102 is located in the motor cortex (M1) and the remote cell population 110 is located in the thalamus.

The resultant images 114 shows the scan results for two slices, 1 and 2, in the thalamus. The images 114 depict the blood oxygenation level-dependent (BOLD) signals elicited in response to excitation of the target cell population 102 with light.

Figure 1B:
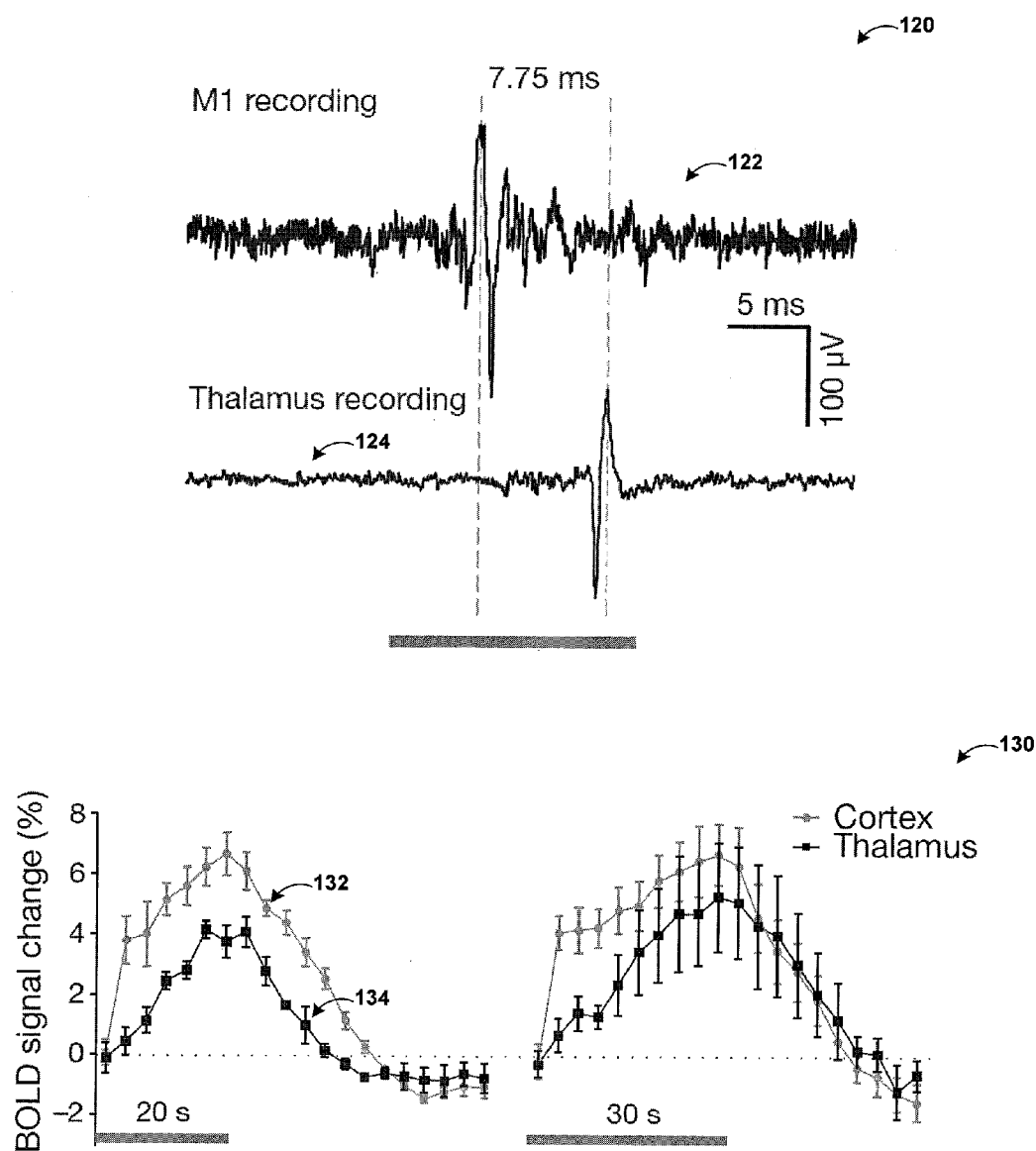
FIG. 1B shows the response of the excited cells in FIG. 1A, in accordance with an example embodiment of the present disclosure.

Turning to FIG. 1B, the responses of the target cell population 102 and the remote cell population 110 are depicted. The top graph 120 shows a recording of the electrical response to light stimulation at the location of the target cell population 122 (labeled M1 recording) and the electrical response of the remote cell population 124 (labeled thalamus recording) in response to light stimulation of the target cell population 102. The excitation is shown to have occurred at the target cell population 102 approximately 8 ms before it occurs at the remote cell population 110. The reading depicted in graph 120 was obtained by introducing electrodes at M1 and at the thalamus to verify that the target cell population 102 and the remote cell population 110 respond to the light 104.

Graph 130 depicts the BOLD signal change in response to the light stimulation both at the cortex (the location of the target cell population 102) and at the thalamus (the location of the remote cell population 110). The cortex response 132 initiates earlier than the thalamus response 134, consistent with the delay found in graph 120.

Figure 2A:
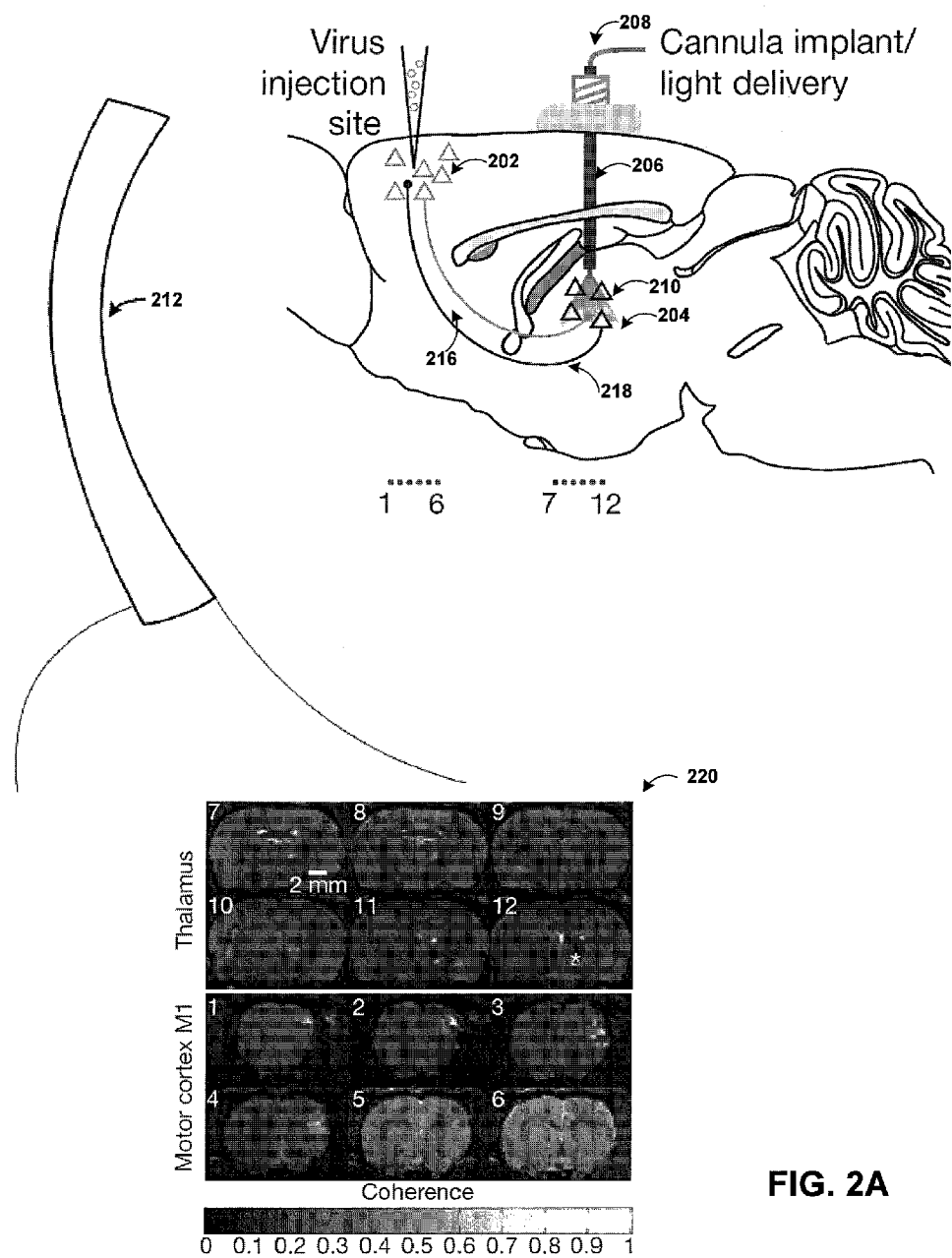
FIG. 2A shows a brain subjected to an ofMRI, in accordance with an example embodiment of the present disclosure.

Turning to FIG. 2A, a method consistent with an embodiment of the present disclosure is depicted. A virus containing a sequence for expressing a light-responsive molecule, such as ChR2, is injected into target cell population 202. A cannula 206 is implanted in a second region of the brain so that optical fiber 208 can provide light 204 to remote cell population 210. The light at the remote location excites the axon projections 216 of the cells 202 that connect to the cells in the remote location. The axon projections 218 of the remote cell population 210 also potentially connect the two cell populations. This results in a BOLD response both at the target cells 202 and the remote cells 210. This also permits functional mapping of the cells in the two areas. An MRI machine 212 is used to collect fMRI scans 220 showing a BOLD response both at the injection site (slices 1-6) and at the site of stimulation (slices 7-12).

Figure 2B:
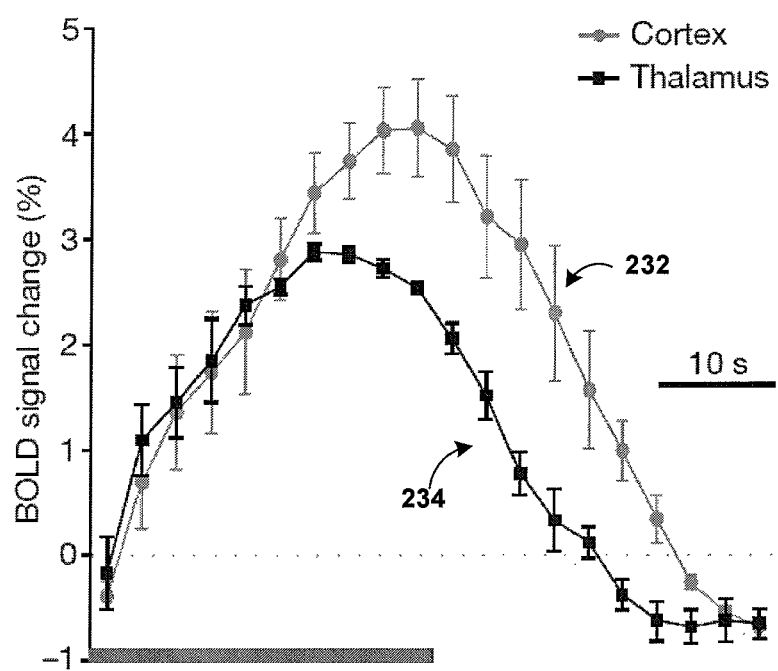
FIG. 2B shows the response of the excited cells in FIG. 2A, in accordance with an example embodiment of the present disclosure.

In certain more specific embodiments, the virus injection site is in the cortex and the light stimulation is provided to the thalamus. FIG. 2B depicts the percentage of BOLD signal change in response to the stimulation. As shown in the figure, the time delay between the response at the thalamus and the motor cortex is lessened. In addition, the BOLD response ramps up more slowly in both the thalamus and the cortex in this embodiment. The fMRI scans 220, along with the BOLD responses 232 and 234 of FIG. 2B indicate that the axon projections 218 were not activated and the remote cell population 210 was not excited by the light, while the axon projection 216 was excited.

Figure 3A:
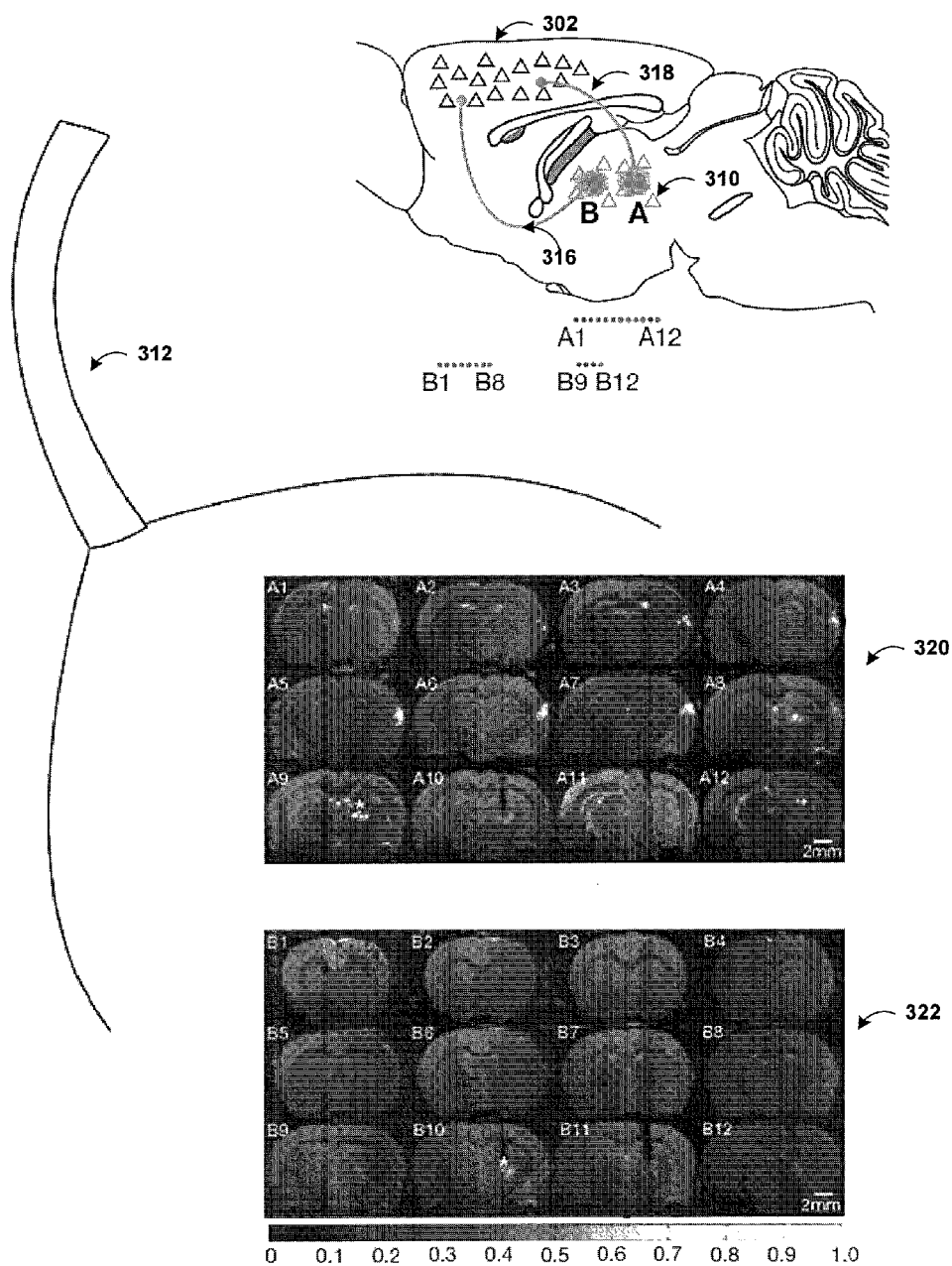
FIG. 3A shows an fMRI of neurons modified to react to light, in accordance with an example embodiment of the present disclosure.

Consistent with an embodiment of the present disclosure, FIG. 3A depicts a scan series wherein a viral vector is injected into the thalamus 310. The viral vector is cell type specific and introduces a light-responsive molecule into specific cells of the thalamus. A cannula provides access to the injection site for an optical fiber. The optical fiber is used to excite the thalamic nuclei that have been infected with the light-responsive molecules. The optical fiber is used to provide light to either posterior thalamic nuclei (a) or anterior thalamic nuclei (b). Projection 318 extends from group A to cells within a remote cell population 302. Projection 316 extends from group B in the thalamic nuclei to remote cell population 302. In certain specific embodiments, remote cell population 302 is located in the motor cortex. Scanning the brain during stimulation by fMRI 312 results in coronal slices 320 being obtained when the posterior thalamic nuclei are excited and slices 322 when the anterior thalamic nuclei are excited.

Figure 3B:
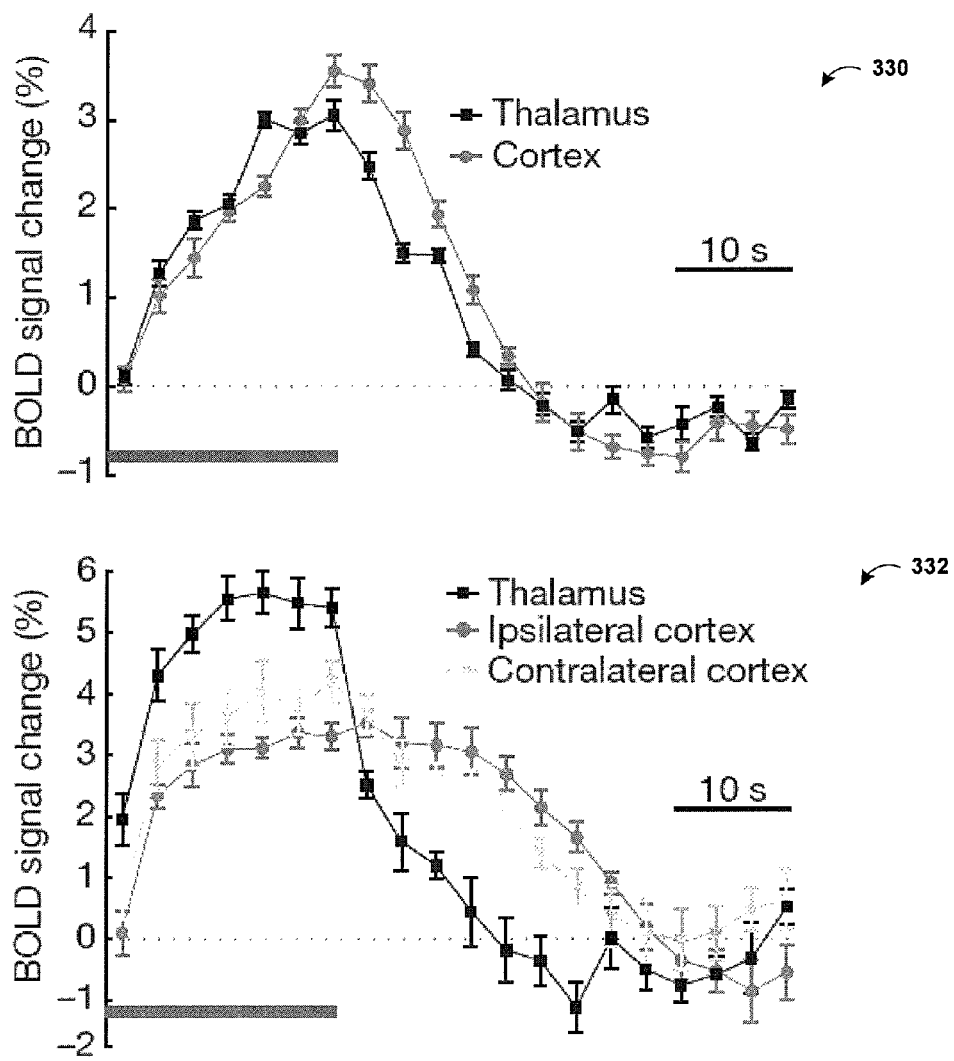
FIG. 3B shows the response of the cells in FIG. 3A, in accordance with an example embodiment of the present disclosure.

FIG. 3B depicts graphs of the percentage of signal change in the BOLD response. Graph 330 corresponds to excitation of the posterior thalamus. Graph 332 corresponds to excitation of the anterior thalamus. Coronal slices 322 and Graph 332 indicate that excitation of anterior thalamic nuclei results in excitation in the thalamus (at the site light is provided), and both the ipsilateral cortex and the contralateral cortex. This is consistent with the anterior thalamus being significant in motor control and coordination.

The above embodiments can be used individually or together to provide functional mapping of the brain. In certain embodiments both the motor cortex and the thalamus are infected with light-responsive molecules that respond to different wavelengths of light. This allows for forward and backward mapping of the connections between cells in the cortex and the thalamus. Further, light of one wavelength can be provided at a site in the thalamus to excite the axon projections of the target cell population in the motor cortex to provide a map of the connections between the target cell population and cells in the thalamus. Light of a second wavelength can be used to stimulate thalamic cells and determine functional connections of the thalamus cells based on the axon projections of the thalamic cells. The thalamic cells infected with the light-responsive molecules responsive to a second wavelength of light can be the same cells that were activated by the motor cortex infected cells. In an alternative embodiment the thalamic cells infected can be different cells.

Certain embodiments consistent with the present disclosure can be useful for determining the progression of a degenerative disease. fMRI scans obtained over time can be compared to determine the presence of deteriorating function. The fMRI scans can also be used to determine if new connections are being made in response to damage to previous connections.

In certain embodiments the fMRI scans can be used to determine the effectiveness of a drug. For example, fMRI scans can be taken before and after administration of a drug intended to alter the functional responsive of a target cell population. The scans can be compared to determine whether the drug has produced the intended result, and if not, the dose of the drug can be adjusted based on the observations of the fMRI scans.

Figure 4:
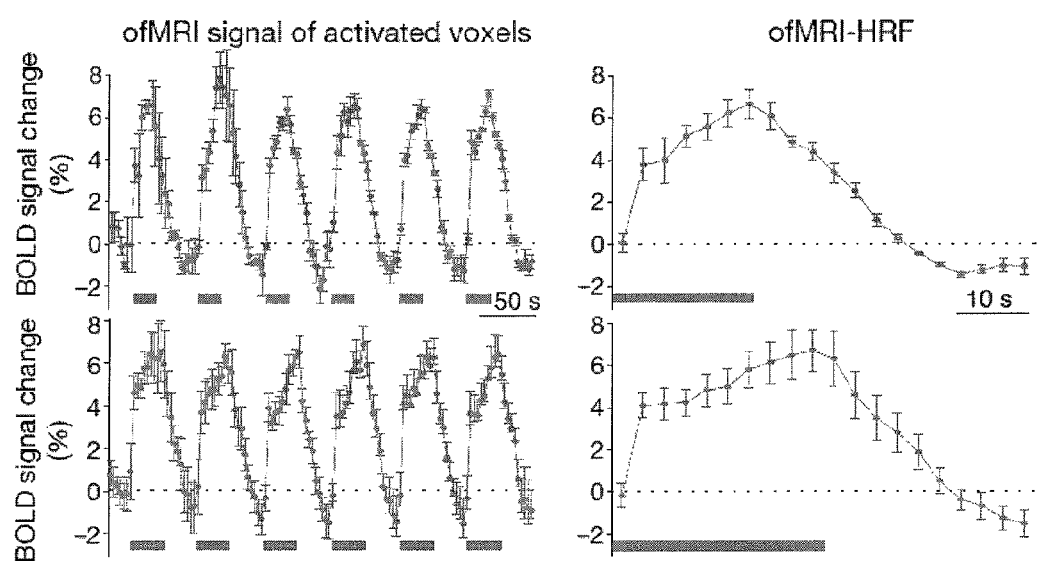
FIG. 4 shows the BOLD and ofMRI-HRF (haemo-dynamic) responses of a target cell population, in accordance with an example embodiment of the present disclosure. ofMRI haemodynamic response (averaged across activated voxels in motor cortex) during 20 s (top) and 30 s (bottom) optical stimuli (Left) is shown and also depicted are mean over stimulus repetitions; baseline, mean pre-stimulation signal (Right). Top panels, n=3; bottom panels, n=8.

In certain embodiments of the present disclosure, the results of the fMRI scans are used to confirm the trigger of the BOLD response depicted in the fMRI slices. In such embodiments, light pulses are delivered to targeted neurons. The BOLD signals from a fMRI scan of the neurons, after they have been infected with a light-responsive molecule while a light pulse is being delivered to the neurons, is compared to a fMRI scan of the same neurons prior to infection with the light pulse being delivered. In such instances no detectable BOLD signal could be elicited from the neurons prior to infection. However, after infection a robust BOLD signal was observed in response to the light pulse. Further, the BOLD dynamics observed by optically driving the cell population expressing the light-responsive molecule match the dynamics of conventional stimulus-evoked BOLD-fMRI. In particular, as depicted in FIG. 4, the optogenetic fMRI haemodynamic response function (ofMRI-HRF) signal onset occurred after 3 seconds but within 6 seconds of stimulus onset. Likewise, offset was reflected by a drop in BOLD signal contrast beginning within 6 seconds and returning to baseline in approximately 20 seconds after optical stimulation. The pronounced post-stimulus undershoot observed during systemic somatosensory stimulation in humans and animals was observed in ofMRI-HRFs as well. All of these dynamic properties derived from driving a defined, specific cell population, correspond closely to previous measurements on conventional sensory-evoked BOLD.

In various embodiments consistent with the present disclosure, neurons are infected with light-responsive molecules as discussed with respect to FIGS. 1A, 2A, and 3A. The activation of the light-responsive molecules can be used to determine the correlation between neuron firing and observed responses for a variety of neural scanning devices or procedures. The scanning includes, but is not limited to: MRI, computed tomography (CT), electroencephalography (EEG), and positron emission tomography (PET).

In certain embodiments more than one type of a light-responsive molecule is introduced into the brain. The light-responsive molecule can be one of several opsins and channelrhodopsins including, but not limited to, VChR1, optoXRs, SFOs, and ChR2 for excitation/modulation of cell in response to specific wavelengths of light, and NpHR, BR, AR, and GtR3 for inhibition of cells in response to specific wavelengths of light. In certain embodiments, the light-responsive molecule is introduced into the brain by a viral vector (such as an AAV) encoding the light-responsive molecule.

EXAMPLES

Despite a rapidly-growing scientific and clinical brain imaging literature based on functional magnetic resonance imaging (fMRI) using blood oxygenation level-dependent (BOLD)' signals, it remains controversial whether BOLD signals in a particular region can be caused by activation of local excitatory neurons. This difficult question is central to the interpretation and utility of BOLD, with major significance for fMRI studies in basic research and clinical applications. Using a novel integrated technology unifying optogenetic control of inputs with high-field fMRI signal readouts, we show here that specific stimulation of local CaMKIIn-expressing excitatory neurons, either in the neocortex or thalamus, elicits positive BOLD signals at the stimulus location with classical kinetics. We also show that optogenetic fMRI (ofMRI) allows visualization of the causal effects of specific cell types defined not only by genetic identity and cell body location, but also by axonal projection target. Finally, we show that ofMRI within the living and intact mammalian brain reveals BOLD signals in downstream targets distant from the stimulus, indicating that this approach can be used to map the global effects of controlling a local cell population In this respect, unlike both conventional fMRI studies based on correlations and fMRI with electrical stimulation that will also directly drive afferent and nearby axons, this ofMRI approach provides causal information about the global circuits recruited by defined local neuronal activity patterns. Together these findings provide an empirical foundation for the widely-used fMRI BOLD signal, and the features of ofMRI define a potent tool that may be suitable for functional circuit analysis as well as global phenotyping of dysfunctional circuitry.

Blood oxygenation level-dependent functional magnetic resonance imaging (BOLD fMRI) is a widely used technology for non-invasive whole brain imaging. BOLD signals reflect complex and incompletely understood changes in cerebral blood flow (CBF), cerebral blood volume (CBV), and cerebral metabolic rate of oxygen consumption ($CMRO_2$) following neuronal activity. Candidate circuit elements for triggering various kinds of BOLD signals include excitatory neurons, mixed neuronal populations, astroglia, and axonal tracts or fibres of passage. Importantly, it is not clear which kinds of activity are capable of triggering BOLD responses, placing limitations on interpretation for both clinical and scientific applications. For example, it is sometimes assumed that positive BOLD signals can be triggered by increased activity of local excitatory neurons, but this remains to be shown empirically, a challenge that seriously confounds fMRI interpretation. Moreover, the use of MRI-compatible electrodes for local stimulation, although of pioneering significance, will nevertheless drive all local excitatory, inhibitory, and modulatory cell types, as well as antidromically drive non-local cells that happen to have axons within the stimulated region, thereby confounding functional circuit mapping using BOLD. We sought to address these challenges by integrating high-field fMRI output with optogenetic stimulation, in which single-component microbial light-activated transmembrane conductance regulators are introduced into specifically targeted cell types and circuit elements'" using cell type-specific promoters to allow millisecond-scale targeted activity modulation in vivo.

Materials and Methods

Virus-Mediated Opsin Expression

In adult rats, the primary motor cortex (M1) was injected with the adeno-associated viral vector AAV5-CaMKIIα::ChR2(H134R)-EYFP to drive expression of a channelrhodopsin (ChR2) specifically in Ca2+/calmodulin-dependent protein kinase II α (CaMKIIα)-expressing principal cortical neurons, but not in GABAergic or glial cells. The pAAV-CaMKIIα-hChR2(H134R)-EYFP plasmid was designed and constructed by standard methods and packaged as AAV5. The pAAV-CaMKIIα-ChR2(H134R)-EYFP plasmid was constructed by cloning CaMKIIα-ChR2(H134R)-EYFP into an AAV backbone using MluI and EcoRI restriction sites. The recombinant AAV vectors were serotyped with AAV5 coat proteins and packaged by the viral vector core at the University of North Carolina; titers were $2 \times 10^{12}$ particles/mL for both viruses. The virus was stereotaxically injected and cannulas placed at the locations where optical stimulation was planned. Concentrated virus was delivered using a 10-μl syringe and 34-gauge needle; volume and flow rate (0.1 μl min$^{-1}$) were controlled by injection pump. Maps and clones are available at www.optogenetics.org.

Female adult (>10 weeks old) Fischer and Sprague-Dawley (250-350 g) rats were the subjects; animal husbandry and all aspects of experimental manipulation were in strict accord with guidelines from the National Institute of Health and have been approved by members of the Stanford Institutional Animal Care and Use Committee (IACUC). Rats were anaesthetized using 1.5% isoflurane (for surgeries longer than 1 hr) or i.p. injection (90 mg/kg ketamine and 5 mg/kg xylazine). The top of the animal's head was shaved, cleaned with 70% ethanol and betadine and then positioned in the stereotactic frame. Ophthalmic ointment was applied, a midline scalp incision was made, and small craniotomies were performed using a drill mounted on the frame. Four types of surgeries were conducted: I) viral injection (1 μl/site) and cannula (1.5 mm projection) placement in M1 (+2.7 mm AP, +3.0 mm ML right hemisphere, two injections at −2.0 and −2.5 mm DV); II) 4 viral injections across cortex (1: +5.2 mm AP, +2.0 mm ML right hemisphere, one 2 μl injection at −3.0 DV; 2: +3.2 mm AP, +3.5 mm ML right hemisphere, 3 injections each 0.7 μl at −3.5 mm, −3.0 mm, and −2.5 mm DV; 3: +2.7 mm AP; +0.5 mm ML right hemisphere; 2 injections 1 μl each at −3.0 mm and −2.5 mm DV; 4: −0.3 mm AP; +3.0 mm ML right hemisphere; 2 injections 1 μl each at −2.5 mm and −2.0 mm DV; and the cannula (6.5 mm projection) was placed in ventral thalamus at the border with ZI (−4.3 mm AP; +2 mm ML right hemisphere; −6.5 mm DV); III) viral injection (1 μl/site) and cannula (5.25 mm projection) placement in thalamus (+2.7 mm AP, +3.0 mm ML right hemisphere, two injections at −5.25 and −5.75 mm DV). IV) Doublefloxed inverted-open reading frame (DIO) ChR2-EYFP was injected stereotactically into the motor cortex (2.0 mm AP; 1.42 mm ML, two injections at −1.25 mm and −1.75 mm DV) of 5-10-week-old transgenic mice expressing Cre recombinase in fast-spiking parvalbuminexpressing GABAergic interneurons (PV::Cre).

Concentrated virus was delivered using a 10 μl syringe and a thin 34 gauge metal needle; injection volume and flow rate (0.1 μl/min) were controlled with an injection pump. After the final injection, the needle was left in place for 5 additional minutes and then slowly withdrawn. An MRI compatible cannula fiber guide (8IC313GPKXXC) was inserted through the craniotomy. One layer of adhesive cement followed by cranioplastic cement was used to secure the fiber guide system to the skull. After 10 min, the scalp was sealed using tissue adhesive. The animal was kept on a heating pad during recovery from anesthesia. Buprenorphine (0.03 mg/kg) was given subcutaneously following the surgical procedure to minimize discomfort. A dummy cannula (8IC312DCSPCC) was inserted to keep the fiber guide patent.

To avoid scanning animals with damage associated with the cannula implantation, detailed anatomical MRI scans were performed to check for tissue damage. In cases where damage near the cannula was detected in the T2 weighted high-resolution anatomical images, animals were rejected and not used in experiments. Moreover, animals used for fMRI studies were examined post-mortem for local invasion and for gliosis, using DAPI and GFAP staining. GFAP is a sensitive marker for gliosis and can report changes in local glial number, glial activation, and inflammation. In all subjects used for fMRI, we did not see evidence for cellular invasion or for gliotic changes (See Supplementary FIG. 1 of "Global and local fMRI signals driven by neurons defined optogenetically by type and wiring," Nature, Vol. 465, 10 Jun. 2010, pp, 788-792) beyond the expected 30-50 μm from the cannula, indicating that the boundaries of the BOLD responses are not determined by local damage or gliosis under these conditions.

Opsin Expression Validation

To validate specificity, sensitivity and spatial distribution of opsin expression, brain slices were prepared for optical microscopy and immunohistochemistry. Coronal sections (40-μm thick) were cut on a freezing microtome and stored in cryoprotectant (25% glycerol, 30% ethylene glycol, in PBS) at 4° C. until processed for immunohistochemistry. Confocal fluorescence images were acquired on a scanning laser microscope using a 20×/0.70NA or a 40×/1.25NA oil immersion objective, while large field images of entire slices were collected on a Leica MZ16FA stereomicroscope.

Immunohistochemistry

To verify the phenotype of cells, rodents were anaesthetized with 65 mg/kg sodium pentobarbital and transcardially perfused with ice-cold 4% paraformaldehyde (PFA) in PBS (pH 7.4). Brains were fixed overnight in 4% PFA and then equilibrated in 30% sucrose in PBS. 40 μm-thick coronal sections were cut on a freezing microtome and stored in cryoprotectant (25% glycerol, 30% ethylene glycol, in PBS) at 4° C. until processed for immunohistochemistry. Free-floating sections were washed in PBS and then incubated for 30 min in 0.2% Triton X-100 (Tx100) and 2% normal donkey serum (NDS). Slices were incubated overnight with primary antibody in 2% NDS (Mouse anti-CaMKIIα 1:500, Abcam, Cambridge, Mass.; Mouse anti-Parvalbumin 1:500, Sigma, St Louis, Mo.; Rabbit anti-GABA 1:500, Millipore, Billerica, Mass.; Chicken anti-GFAP 1:250, Millipore; Mouse anti-MAP2 1:500, Sigma). Sections were then washed with PBS and incubated for 2 hr at RT with secondary antibodies (Donkey anti-Mouse conjugated to either Cy3 or FITC, donkey anti-Rabbit Cy5 and donkeyanti chicken Cy5, all 1:1000, Jackson Laboratories, West Grove, Pa.). Slices were then washed, incubated with DAPI (1:50,000) for 20 min, washed again, and mounted on slides with PVA-Dabco (Sigma). Confocal fluorescence images were acquired on a scanning laser microscope using a 20×/0.70NA or a 40×/1.25NA oil immersion objective.

In Vivo Optical Stimulation

20 Hz, 15 ms pulsewidth stimulation with 473 nm light was used for all fMRI and optrode recordings. 300 μm diameter optical fibers were used with the optical fiber output power level at approximately 6 mW. These power levels correspond to 85 mW mm$^{-2}$ at the fiber output, but more than 10-fold less over the majority of the excitation volume given the expected light scattering profile. Assuming 1 mW/mm$^2$ is the minimum light power needed to activate ChR2, the light penetration depth of direct light activation is expected to be ~0.95 mm. Optical stimulation power must be set with care in order to avoid potential BOLD signal confound due to heating; we have found that at higher laser power levels or with steady illumination, laser synchronized signal intensity change can be observed even in control animals; the BOLD sequence, which gives $T_2^*$-weighting has been found to have no significant temperature dependence at lower temperatures, while high enough temperature causing tissue damage has been found to result in signal amplitude decrease. Therefore, it was decided to use ≤~6 mW of laser power and maintained pulsed waveforms with 30% duty cycle.

Analysis of Electrophysiological Data

Threshold search in Clampfit was used for automated detection of spikes in multi-unit recording, which was then validated by visual inspection. For traces with multiple spike populations, thresholds were set to capture all the spikes; during bursting, it is likely that multiple neurons were recorded from simultaneously.

Optogenetic fMRI

Rodent subjects were connected to the optical fiber and ventilator (1.3% isoflurane), physiological monitoring systems and radio-frequency coil, and placed in the magnetic resonance-compatible stereotaxic frame. After subject placement in the scanner, blue (473 nm) light pulsed at 20 Hz (15 ms pulse width) was periodically applied through the optical fiber at 1 min intervals while repeated BOLD scans of large brain volumes were conducted.

fMRI scans were conducted with a small animal dedicated MRI scanner, custom designed pulse sequences, RF coils, and cradle. The small animal scanner consisted of a Magnex scientific superconducting magnet with 7.0 Tesla (T) field strength, RRI gradient with clear bore size of 9 cm, maximum gradient amplitude of 770 mT/m and maximum slew rate of 2500 T/m/s and a General Electric (GE) console and radiofrequency (RF) amplifiers with maximum RF amplitude of 24.7 μT. The animals were first anesthetized in a knockdown box with 4% isoflurane. After approximately 5 minutes in the knockdown box, the animal was intubated, placed on a custom-designed MRI-compatible cradle with a stereotaxic frame, and the tracheal tube connected to a ventilator (Harvard Apparatus, Model 683 Small Animal Ventilator) with 1.3-1.5% isoflurane, 35% $O_2$, 65% $N_2O$ input gas and a capnometer (SurgiVet V9004). A 3.5 cm diameter custom-designed transmit/receive single-loop surface coil was placed on the top of the target, and a 300 μm diameter optical fiber was then inserted through the guide. A fiber-optic rectal temperature probe was inserted and the cradle with the animal was inserted to the isocenter of the magnet. Expiratory CO2 content was continuously monitored by a capnometer. The ventilation volume and frequency (3.0-3.5 cc/stroke, 50-60 stroke/min) was controlled to keep the endtidal $CO_2$ level at ~3.5% throughout the scan. Heated air was pumped into the bore to maintain animal's body temperature at physiological levels (34-38° C.).

fMRI scans were performed using conventional GRE-BOLD fMRI methods and passband b-SSFP fMRI4 methods. Passband bSSFP-fMRI was designed to be a 3D volumetric, b-SSFP sequence with stack-of-spirals readout trajectory. To get good slab selection for the passband bSSFP-fMRI scans, a time-bandwidth (TBW) of 12 pulse was designed with a duration of 1 ms. 10 interleave in-plane spirals with 32 stack locations, 9.372 ms TR, 2 ms TE resulted in 30 slices (2 slices discarded due to 3D slice direction excitation profile roll-off margin) and 1.5 cm slice direction volume coverage.

fMRI data was first reconstructed through a 2-dimensional (2D) and 3D gridding reconstruction methods. The reconstructed 4D magnitude image data was then analyzed by calculating the individual voxel coherence value (c), defined as the magnitude of the frequency component of interest ($|F(f_0)|$) divided by the sum-of-squares of all frequency components:

$$\sqrt{\Sigma_f |F(f)|^2}; F:$$

(Fourier transform of temporal signal intensity; $f_0$: frequency of stimulation—here, 1/60 Hz). Therefore, the coherence value (c) is between 0 and 1. The coherence value was thresholded at 0.35, color coded and overlaid onto $T_2$ anatomical images:

$$c = \frac{|F(f_0)|}{\sqrt{\Sigma_f |F(f)|^2}}$$

Coherence values (c) can be converted to z- and p-values given the mean (m), variance ($\sigma^2$) of the null-hypotheses distribution. The following formula can be used to calculate the corresponding z value given the c value, m, σ, and N (sample size for estimation of m and σ).

$$z = \frac{1}{\sigma}\left(\sqrt{\frac{c^2}{(1-c^2)}((N-1)\sigma^2 + Nm^2)} - m\right)$$

The p-value can then be estimated with an assumption for the null-hypothesis. For example, in our study, coherence of 0.35 corresponds to z-value of approximately 4.6, which gives a p-value of approximately 0.000002 when Gaussian distribution is assumed. Therefore, the p-value threshold in all our experiments can be assumed to be less than 0.001. For most of the data, the thresholded coherence value was overlaid onto $T_2$ anatomical images to show "activated" voxels. However, for the PV::Cre stimulation result, since pixels with opposite phase with respect to stimulation were present, color-coded phase values of pixels with coherence level over 0.35 were displayed to show the distribution of positive and negative BOLD. The phase value (θ) was calculated as the phase of the frequency component of interest, resulting in phase values between 0 and 2π (0 corresponds to no delay with respect to stimulus, and π corresponds to the half cycle delay of 30 s in these experiments).

$$θ = \angle(F(f_0))$$

Voxel-based frequency analysis was used as the method with fewest assumptions instead of model-based methods since the HRF of ofMRI was not known.

In Vivo Recording and Analysis

After ofMRI, simultaneous optical stimulation and electrical recording in living rodents was conducted using an optrode composed of an extracellular tungsten electrode (1M Ω, ~125 μm) attached to an optical fiber (~200 mm) with the tip of the electrode deeper than the tip of the fiber to ensure illumination of the recorded neurons.

Simultaneous optical stimulation and electrical recording in living rodents was conducted as described previously using an optrode composed of an extracellular tungsten electrode (1 M Ω, ~125 μm) attached to an optical fiber (~200 μm) with the tip of the electrode deeper (~0.4 mm) than the tip of the fiber to ensure illumination of the recorded neurons. For stimulation and recording in two distinct regions (M1 and thalamus), small craniotomies were created above both target regions. The optical fiber was coupled to a 473 nm laser diode from CrystaLaser. Optrode recordings were conducted in rats anesthetized with 1.5% isoflurane. pClamp 10 and a Digidata 1322A board were used to both collect data and generate light pulses through the fiber. The recorded signal was bandpass filtered at 300 Hz low/5 kHz high (1800 Microelectrode AC Amplifier) and filtered in Clampfit to remove 60 Hz noise. For precise placement of the fiber/electrode pair, stereotactic instrumentation was used.

Results

In these experiments, the cortical virus injection site was also used as the optical stimulation site for BOLD and electrophysiological functional studies (FIG. 5a). To minimize susceptibility artefact during MRI scanning, the implanted cannula, optical fibre and accessories were custom-fabricated from magnetic resonance-compatible materials. Confocal imaging (FIG. 5b) and optrode recording (simultaneous optical stimulation and electrical recording) under 1.3-1.5% isoflurane anaesthesia' (FIG. 5c) were conducted to validate the expression and functionality, respectively, of the ChR2-EYFP (enhanced yellow fluorescent protein) fusion under these conditions. In line with previous optogenetic studies", 473 nm light pulses at 20 Hz (15 ms pulse width) delivered through the optical fibre were found to drive local neuronal firing reliably in vivo (FIG. 5c).

To assess fMRI signals, we acquired 0.5 mm coronal slices centered on M1, >10 days after virus injection (FIG. 5d). Intubated animals were placed on a custom-designed MRI-compatible cradle with a stereotaxic frame and ventilated with 1.3-1.5% isoflurane. A 3.5 cm-diameter custom-designed transmit/receive single-loop surface coil was opposed to the cranium and a long 300-μm diameter optical fibre inserted through the implanted cannula; in this configuration, the cradle with the animal was placed into the isocentre of the magnet while the laser diode itself was maintained outside the 5 Gauss perimeter. To minimize systemic physiological confounds, the ventilation volume, frequency, end-tidal $CO_2$ and rectal temperature levels were carefully maintained at narrow levels known to produce most robust and reproducible BOLD signals in anaesthetized animals (3.0-3.5 $cm^3$ per stroke, 50-60 strokes per min, 3.5%, 34-38° C.). fMRI scans were performed at 7.0 Tesla (T) field strength using conventional gradient-echo (GRE)-BOLD fMRI and pass-band balanced steady-state free precession (b-SSFP)-fMRI. Both pulse sequences were designed to have 3.5×3.5 $cm^2$ in-plane field of view (FOV), 0.5×0.5×0.5 $mm^3$ spatial resolution and 3 s temporal resolution. GRE-BOLD fMRI was designed to be a two-dimensional, multi-slice, gradient-echo sequence with four-interleave spiral readout; 750 ms repetition time (TR) and 12 ms echo time (TE) resulting in 23 slices covering 1.15 cm slice direction volume. This specific design allowed large-volume mapping of the brain during optogenetic control with high temporal resolution.

Light pulses at 20 Hz (473 nm, 15 ms pulse width) were delivered to targeted CaMK1Iix-expressing principal neurons, and in response, robust optically-evoked BOLD signals were observed in cortical grey matter at the virus injection and optical stimulation site, whereas in control animals (injected with saline instead of opsin-AAV) no detectable BOLD signal could be elicited (FIG. 5). Stimulus-synchronized BOLD haemodynamic responses from activated M1 voxels are displayed in FIG. 5d, and mean optogenetic fMRI haemodynamic response functions (ofMRI-HRF) in FIG. 4. Evoked BOLD was dominated by positive signals while driving these excitatory CaMKIIα-positive cells; in contrast, optically driving inhibitory parvalbumin-positive cells, which may have unique connectivity with local neuronal circuitry or vasculature, additionally gave rise to a zone of negative BOLD, consistent with the GABAergic phenotype, surrounding the local positive BOLD signal (See Supplementary FIG. 4 of "Global and local fMRI signals driven by neurons defined optogenetically by type and wiring," Nature, Vol. 465, 10 Jun. 2010, pp, 788-792). Strikingly, the BOLD dynamics observed by optically driving the defined CaMKIIα principal cell population embedded within the mixed M1 cell population precisely matched the dynamics of conventional stimulus-evoked BOLD-fMRI. In particular, the ofMRI-HRF signal onset occurred after 3 s but within 6 s of stimulus onset; likewise offset was reflected by a drop in BOLD signal contrast beginning within 6 s and returning to baseline in ~20 s after optical stimulation (FIG. 4; upper panels: n=3, lower panels: n=8). Finally, the pronounced post-stimulus undershoot observed during systemic somatosensory stimulation in humans and animals was preserved in ofMRI-HRFs as well (FIG. 4). All of these dynamic properties derived from driving a defined, specific (See Supplementary FIG. 1a of "Global and local fMRI signals driven by neurons defined optogenetically by type and wiring," Nature, Vol. 465, 10 Jun. 2010, pp, 788-792) cell population correspond closely to previous measurements on conventional sensory-evoked BOLD.

Figure 6A:
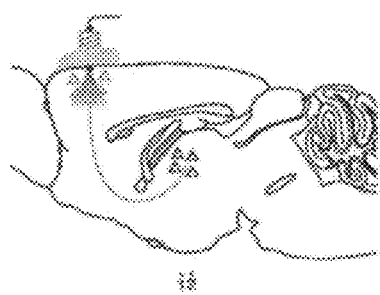
FIG. 6a schematically depicts a variation of a system and method for AAV5-CaMKIIα::ChR2-EYFP injection and optical stimulation in M1. Slices in "c": '1' and '2.
Figure 6B:
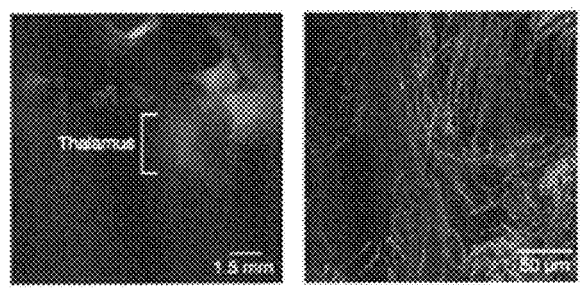
' FIG. 6b shows fluorescence/bright-field images of ChR2-EYFP in thalamus (left); the confocal image (right) shows that expression is limited to axons.
Figure 6C:
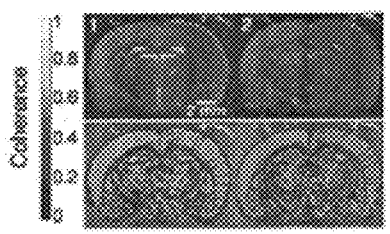
FIG. 6c depicts slices '1' and '2' that were taken at points '1' and '2' of FIG. 3a and shows thalamic ofMRI during M1 optical stimulation (top); superimposed on the Paxinos atlas (bottom).
Figure 6D:
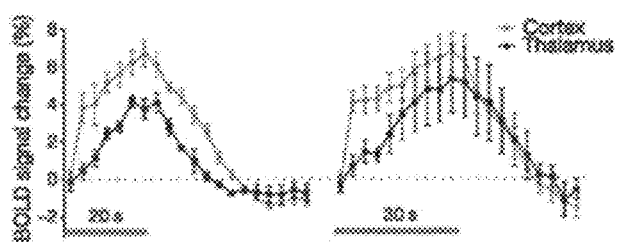
FIG. 6d are plots that summarize ofMRI-HRF results.

To study macrocircuit properties of the brain using optogenetic fMRI, it will be important to assess feasibility of monitoring long-range activity in synaptically connected brain areas. MRI-compatible electrodes for local stimulation represent a major advance but in addition to driving all local excitatory, inhibitory and modulatory cell types, will also antidromically drive non-local cells that happen to have axons within the stimulated region, posing a challenge for functional mapping using BOLD. We therefore used high-resolution fMRI slices capturing thalamic nuclei (coronal slices shown in FIG. 6a) to monitor downstream responses during optical stimulation of M1 cortical neurons. FIG. 6b illustrates the observed specific ChR2 expression in corticothalamic axonal projection fibers whereas thalamic cell bodies showed no ChR2 expression, as expected from the cortical injection protocol (See Supplementary FIG. 5 of "Global and local fMRI signals driven by neurons defined optogenetically by type and wiring," Nature, Vol. 465, 10 Jun. 2010, pp, 788-792). Local optical stimulation was then delivered to the cortex during fMRI, to determine if unidirectionally triggered BOLD responses could be observed and measured (this method eliminates the antidromic drive confound from which electrical stimulation suffers, thereby allowing true global causal connectivity mapping). FIGS. 6c and d summarize the thalamic ofMRI-HRFs; robust thalamic BOLD signals in response to MI stimulation were observed, but with properties quite distinct from the intracortical CaMKIIα+ response described above. A markedly reduced initial rise and slope for onset kinetics of positive-BOLD downstream thalamic recruitment was observed (FIG. 6d, black traces; local cortical BOLD signals shown for comparison, grey traces; cortical BOLD activation is shown in FIG. 5).

Figure 6E:
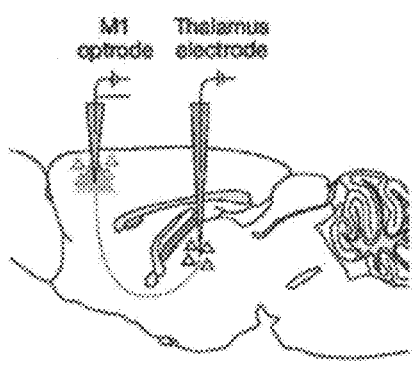
FIG. 6e schematically depicts a M1 optrode and a thalamic electrode.
Figure 6F:
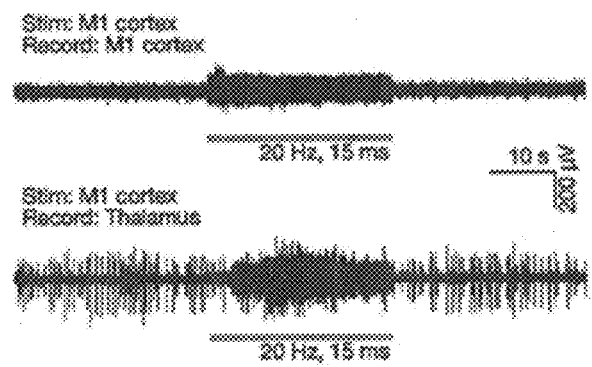
FIG. 6f shows thalamic spiking that follows M1 optical stimulation; delay consistent with BOLD.
Figure 6G:
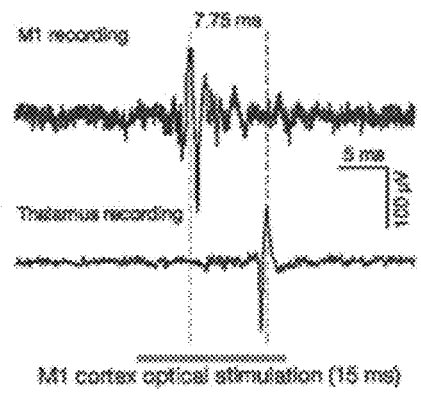
FIG. 6g depicts typical M1 and thalamus spikes that arise with M1 optical excitation.
Figures 6H, 6I:
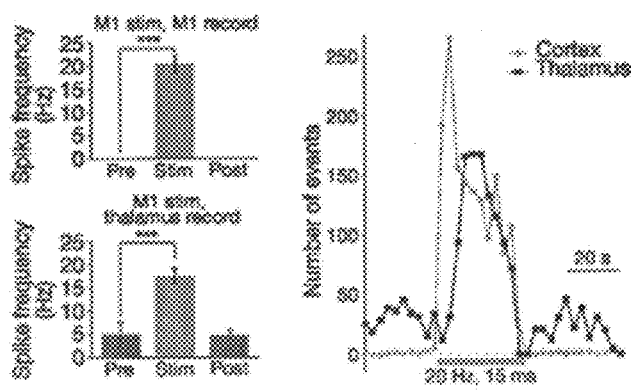
FIG. 6h are histograms that summarize M1 and thalamus spiking profiles (error bar indicates ±s.d., two-sample t-test; *** indicates P<0.001; n=5).
FIG. 6i depicts spike-frequency time histograms.

Given the unusual kinetics, we sought to determine if this delayed thalamic BOLD response would be discrepant with local thalamic electrical activity, assessed with simultaneous optrode stimulating/recording in motor cortex and electrode recoding in thalamus (FIG. 6e). However, a strikingly similar pattern was observed with direct recording in thalamus, including a commensurate delay in spike-rate increase for thalamic neurons compared to cortical neurons during cortical optogenetic drive (FIG. 6f), further supporting the tight correspondence between positive BOLD and local neuronal excitation. Additional characterization showed that after this ~5 s delay presumably related to network properties, successfully evoked spikes recorded in the thalamus reliably followed cortical spikes by several milliseconds, as expected (FIG. 6g). Summary data on mean spike rates is presented in FIG. 6h, and on spike rate dynamics in FIG. 6i; further details on the pass-band bSSFP-fMRI method we developed for small animal imaging with more robust whole-brain mapping capability than traditional BOLD are presented in the Supplementary Material, particularly Supplementary FIG. 3, of "Global and local fMRI signals driven by neurons defined optogenetically by type and wiring," *Nature*, Vol. 465, 10 Jun. 2010, pp, 788-792.

Because true functional outputs of genetically defined neurons in a brain region can be globally mapped with ofMRI (FIG. 6), it is conceivable that additional levels of specificity could also be achieved. For example, M1 excitatory pyramidal neurons form a genetically and anatomically defined class of cell, but within this class are cells that each project to different areas of the brain or spinal cord and therefore have fundamentally distinct roles. Genetic tools may not advance far enough to separate all of these different cell classes, pointing to the need for other promoter-independent targeting methods. But ofMRI raises the current possibility of globally mapping the causal roles of these cells, accessing them by means of connection topology—that is, by the conformation of their functional projection patterns in the brain. We therefore sought to test this possibility by selectively driving the M1 CaMKIIα-expressing cells that project to the thalamus.

Figure 7A:
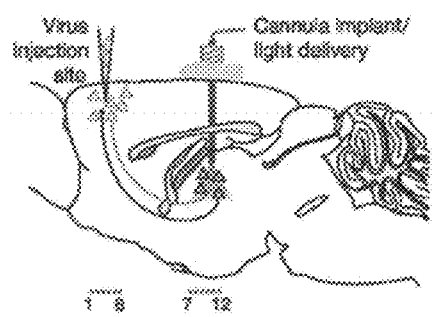
FIG. 7a schematically depicts a variation of a system and method for M1 injection of AAV5-CaMKIIα::ChR2-EYFP and optical stimulation of the thalamus. Coronal slices shown in FIG. 7c marked as '1 . . . 6' and '7 . . . 12'.
Figure 7B:
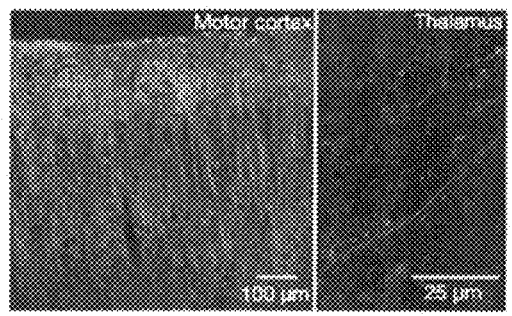
FIG. 7b shows a ChR2 expression pattern confirming expression in cortical neurons (left) and cortico-thalamic projections (right; see also Supplementary FIG. 5 of "Global and local fMRI signals driven by neurons defined optogenetically by type and wiring" *Nature*, Vol. 465, 10 Jun. 2010, pp, 788-792).
Figure 7C:
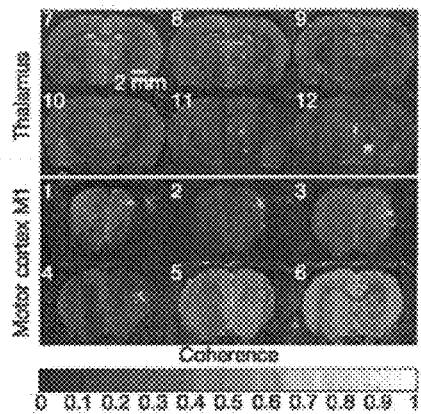
FIG. 7c shows BOLD ofMRI data obtained in thalamus (above) and cortex (below).
Figure 7D:
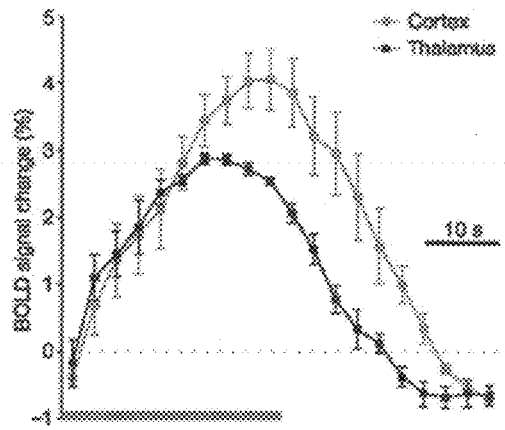
FIG. 7d depicts plots of ofMRI-HRF for cortical (grey) and thalamic (black) BOLD signals elicited by optical stimulation of cortico-thalamic fibers in thalamus. Both of MRI-HRFs ramp slowly by comparison with intra-cortical results in FIG. 5.

An optical fibre was stereotactically placed in the thalamus of animals that had received M1 cortical viral injections (FIG. 7a); post hoc validation (FIG. 7b) confirmed ChR2 expression in cortical neurons and in cortico-thalamic projection fibers. ChR2 readily triggers spikes in illuminated photosensitive axons that both drive local synaptic output and back-propagate throughout the axon to the soma of the stimulated cell; note that unlike the case with electrical stimulation, specificity is maintained for driving the targeted (photosensitive) axons, and therefore this configuration in principle allows ofMRI mapping during selective control of the M1 cortical cells that project to the thalamus. Indeed, robust BOLD signals were observed both locally in the thalamus (FIG. 7c, coronal slices 7-12) and also in M1 (FIG. 7d, coronal slices 1-6), consistent with the anticipated recruitment of the topologically targeted cells both locally and distally. These data demonstrate that ChR2-expressing axonal fibre stimulation alone is sufficient to elicit BOLD responses in remote areas, and illustrate the feasibility for in vivo mapping of the global impact of cells defined not only by anatomical location and genetic identity, but also by connection topology.

Figure 8A:
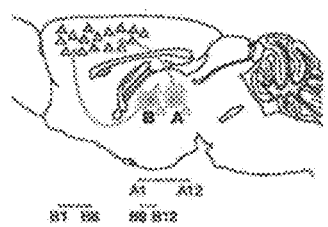
FIG. 8a schematically depicts a variation of a system and method for thalamic injection of AAV5-CaMKIIα::ChR2-EYFP and posterior/anterior optical stimulation. Coronal slices marked 'A1 . . . A12' and 'B1 . . . B12'.
Figure 8B:
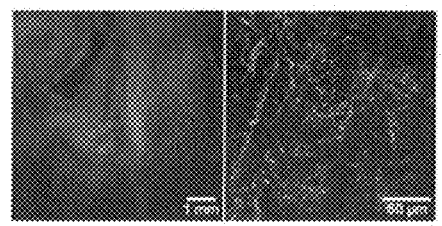
FIG. 8b depicts an image where fluorescence is overlaid onto bright-field (left) and confocal image (right) illustrating transduction in the thalamus (left) and cortical projections in the internal and external capsule (right).
Figure 8C:
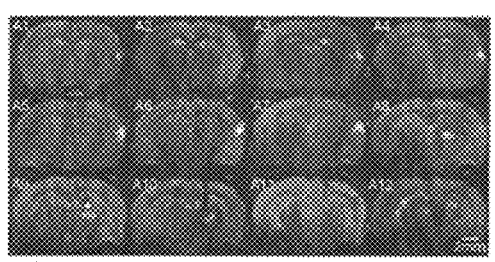
FIG. 8c depicts scans of posterior thalamus stimulation-evoked ofMRI signal in the ipsilateral thalamus and somatosensory cortex.
Figure 8D:
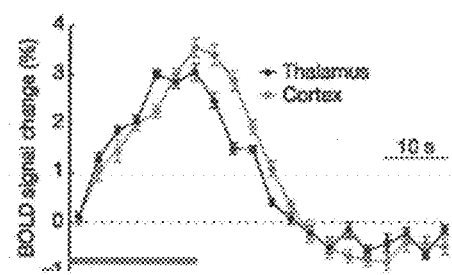
FIG. 8d is a plot of ofMRI-HRFs. Excited volumes: 5.5±1.3 mm$^3$ (thalamus); 8.6±2.5 mm$^3$ (somatosensory cortex) (n=3).
Figure 8E:
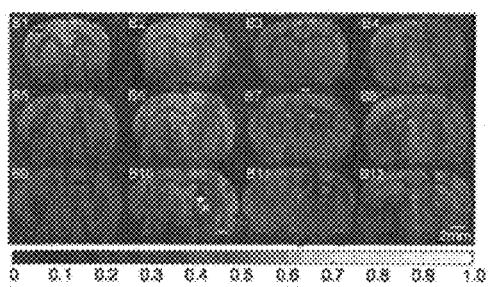
FIG. 8e depicts scans of anterior thalamus stimulation-evoked ofMRI signal in the ipsilateral thalamus and bilateral motor cortex.
Figure 8F:
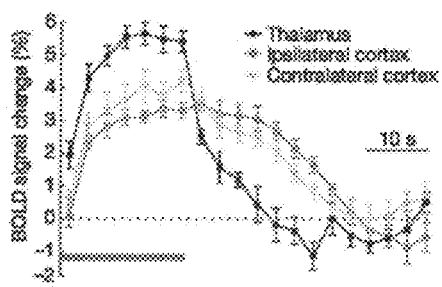
FIG. 8f is a plot of ofMRI-HRFs. Excited volumes: 1.5 mm3 (thalamus); 10.1 mm3 (ipsilateral cortex); 3.7 mm3 (contralateral cortex).

We further explored the global mapping capabilities of ofMRI. It has been suggested that thalamic projections to the motor cortex may be more likely than those to the sensory cortex, to involve both ipsilateral and contralateral pathways, because in many cases motor control and planning must involve bilateral coordination. This principle is challenging to assess at the functional level, because electrode-based stimulation will drive antidromic as well as orthodromic projections, and hence may mistakenly report robust cortico-thalamic rather than thalamocortical projections. We therefore sought to globally map functional connectivity arising from the initial drive of anterior or posterior thalamic nucleus projections, using ofMRI. After injecting CaMKIIα::ChR2 into the thalamus (FIG. 8), we found that optical stimulation of posterior thalamic nuclei resulted in a strong BOLD response, both at the site of stimulation as expected and in the posterior ipsilateral somatosensory cortex (S2) (FIG. 8a-d). Optically stimulating excitatory cell bodies and fibres in the more anterior thalamic nuclei resulted in BOLD response at the site of stimulation and also significant ipsilateral and contralateral cortical BOLD responses (FIG. 8e, f), consistent with the proposed bilaterality of anterior thalamocortical nuclei involvement in motor control and coordination Together, these results illustrate the power of optogenetic fMRI in shedding light on the controversial identification of positive BOLD signals with increased local neuronal excitation, providing an empirical underpinning for fMRI BOLD. We also find that the properties of integrated optogenetics and BOLD-fMRI (ofMRI) allow for global mapping of the causal connectivity of defined neurons in specific brain regions, fundamentally extending the capabilities of pharmacological or electrode-based methods (of course, contributions from additional cells and processes downstream of the defined optically-triggered population are expected and indeed represent an important aspect of this approach; it is, however, important to note that absence of a BOLD signal does not prove the absence of connectivity). Finally, we demonstrate that ofMRI allows causal connectivity mapping of cells defined not only genetically but also by circuit topology, or the conformation of their connections in vivo. Together, the ofMRI methods and findings reported here provide tools and approaches for further probing and defining the causal generation of BOLD signals; these results may accelerate the search for global circuit-disease endophenotypes, as well as the dynamical mapping and reverse engineering of intact neural circuitry.

The skilled artisan would understand that various steps and articles disclosed above for such embodiments can be used selectively to effect different but related embodiments.

While the present disclosure is amenable to various modifications and alternative forms, specifics thereof have been shown by way of example in the drawings and will be described in further detail. It should be understood that the intention is not to limit the disclosure to the particular embodiments and/or applications described. On the contrary, the intention is to cover all modifications, equivalents, and alternatives falling within the spirit and scope of the present disclosure.

REFERENCES

Ogawa, S. et al. Intrinsic signal changes accompanying sensory stimulation: Functional brain mapping with magnetic resonance imaging. *Proc. Natl Acad. Sci. USA* 89, 5951-5955 (1992).

Logothetis, N. K., Pauls, J., Augath, M., Trinath, T. & Oeltermann, A. Neurophysiological investigation of the basis of the fMRI signal. *Nature* 412, 150-157 (2001).

Cohen, J. D. & Blum, K. I. Reward and decision. *Neuron* 36, 193-198 (2002).

Boyden, E. S., Zhang, F., Bamberg, E., Nagel, G. & Deisseroth, K. Millisecondtimescale, genetically targeted optical control of neural activity. *Nature Neurosci.* 8, 1263-1268 (2005).

Zhang, F., Wang, L. P., Boyden, E. S. & Deisseroth, K. Channel rhodopsin-2 and optical control of excitable cells. *Nature Methods* 3, 785-792 (2006).

Deisseroth, K. et al. Next-generation optical technologies for illuminating genetically targeted brain circuits. *J. Neurosci.* 26, 10380-10386 (2006).

Zhang, F. et al. Multimodal fast optical interrogation of neural circuitry. *Nature* 446, 633-639 (2007).

Zhang, F., Aravanis, A. M., Adamantidis, A., de Lecea, L. & Deisseroth, K. Circuit-breakers: optical technologies for probing neural signals and systems. *Nature Rev. Neurosci.* 8, 577-581 (2007).

Aravanis, A. M. et al. An optical neural interface: in vivo control of rodent motor cortex with integrated fiberoptic and optogenetic technology. *J. Neural Eng.* 4, S143-S156 (2007).

Sohal, V. S., Zhang, F., Yizhar, O. & Deisseroth, K. Parvalbumin neurons and gamma rhythms enhance cortical circuit performance. *Nature* 459, 698-702 (2009).

Gradinaru, V., Mogri, M., Thompson, K. R., Henderson, J. M. & Deisseroth, K. Optical deconstruction of parkinsonian neural circuitry. *Science* 324, 354-359 (2009).

Zhang, F. et al. Optogenetic interrogation of neural circuits: technology for probing mammalian brain structures. *Nature Protocols* 5, 439-456 (2010).

Gradinaru, V. et al. Molecular and cellular approaches for diversifying and extending optogenetics. *Cell* 141, 154-165 (2010).

Friston, K. J. Functional and effective connectivity in neuroimaging: a synthesis. *Hum. Brain Mapp.* 2, 56-78 (1994).

Uğurbil, K. et al. Functional mapping in the human brain using high magnetic fields. *Phil. Trans. R. Soc. Lond. B* 354, 1195-1213 (1999).

Logothetis, N. K. What we can do and what we cannot do with fMRI. *Nature* 453, 869-878 (2008).

Douglas, R. J. & Martin, K. A. A functional microcircuit for cat visual cortex. *J. Physiol.* (Lond.) 440, 735-769 (1991).

Sirotin, Y. B. & Das, A. Anticipatory haemodynamic signals in sensory cortex not predicted by local neuronal activity. *Nature* 457, 475-479 (2009).

Cauli, B. et al. Cortical GABA Interneurons in neurovascular coupling: relays for subcortical vasoactive pathways. *J. Neurosci.* 24, 8940-8949 (2004).

Masamoto, K., Kim, T., Fukuda, M., Wang, P. & Kim, S. G. Relationship between neural, vascular, and BOLD signals in isoflurane-anesthetized rat somatosensory cortex. *Cereb. Cortex* 17, 942-950 (2007).

Lee, J. H. et al. Full-brain coverage and high-resolution imaging capabilities of passband b-SSFP fMRI at 3T. *Magn. Reson. Med.* 59, 1099-1110 (2008).

Lee, J. H., Hargreaves, B. A., Hu, B. S. & Nishimura, D. G. Fast 3D imaging using variable-density spiral trajectories with applications to limb perfusion. *Magn. Reson. Med.* 50, 1276-1285 (2003).

Glover, G. H. & Lee, A. T. Motion artifacts in fMRI: comparison of 2DFT with PR and spiral scan methods. *Magn. Reson. Med.* 33, 624-635 (1995).

Buxton, R. B., Wong, E. C. & Frank, L. R. Dynamics of blood flow and oxygenation changes during brain activation: the balloon model. *Magn. Reson. Med.* 39, 855-864 (1998).

Boynton, G. M., Engel, S. A., Glover, G. H. & Heeger, D. J. Linear systems analysis of functional magnetic resonance imaging in human V1. *J. Neurosci.* 16, 4207-4221 (1996).

Donahue, M. J. et al. Theoretical and experimental investigation of the VASO contrast mechanism. *Magn. Reson. Med.* 56, 1261-1273 (2006).

Lauritzen, M. Reading vascular changes in brain imaging: is dendritic calcium the key? *Nature Rev. Neurosci.* 6, 77-85 (2005).

Nir, Y., Dinstein, I., Malach, R. & Heeger, D. J. BOLD and spiking activity. *Nature Neurosci.* 11, 523-524, author reply 524 (2008).

Alloway, K. D., Olson, M. L. & Smith, J. B. Contralateral corticothalamic projections from MI whisker cortex: potential route for modulating hemispheric interactions. *J. Comp. Neurol.* 510, 100-116 (2008).

Kuramoto, E. et al. Two types of thalamocortical projections from the motor thalamic nuclei of the rat: a single neuron-tracing study using viral vectors. *Cereb. Cortex* 19, 2065-2077 (2009).

---

What is claimed is:

1. A method comprising:
    modifying a target neural cell population in a first region of a brain to express a light-responsive opsin polypeptide using an apparatus for delivering a nucleic acid comprising a nucleotide sequence encoding the light-responsive opsin polypeptide;
    stimulating, using a light source for delivering a light pulse, a second region of the brain not modified to express the light-responsive opsin polypeptide;
    scanning multiple regions of the brain using a functional magnetic resonance imaging device that is configured to observe a neural reaction in response to the stimulation in the second region of the brain; and
    determining whether neural projections in a second region of the brain are connected to at least some of the modified target cell population in the first region of the brain.

2. The method of claim 1, wherein the light source is configured to stimulate the light-responsive opsin polypeptide at a first light pulse rate and a second light pulse rate.

3. The method of claim 1, wherein the first region of the brain is in the motor cortex.

4. The method of claim 1, wherein the observed neural reactions are used to determine a treatment plan for a disease effecting at least one of the first or second regions of the brain.

5. The method of claim 1, further comprising:
    introducing a drug into the brain, and repeating the steps of stimulating the second region of the brain, and scanning multiple regions of the brain; and
    determining the effectiveness of the drug based on a comparison of the observed neural reactions in the scan before the introduction of the drugs and the observed neural reactions in the scan after the introduction of the drug.

6. The method of claim 2, wherein the results of the stimulating at the first light pulse rate and the second light pulse rate are combined, and the method comprises providing a functional map of the brain including at least the results of the stimulating at the first light pulse rate and the second light pulse rate.

7. The method of claim 1, wherein the functional magnetic resonance imaging device is configured to observe a blood oxygenation level-dependent (BOLD) signal response, and wherein the method further comprises inferring a relationship between the BOLD response depicted in the fMRI scan results and the neural cell stimulation.

8. The method of claim 1, further comprising determining whether neural projections in the first region of the brain are connected to neural cells in the second region of the brain.

9. The method of claim 1, wherein the apparatus for delivering the nucleic acid to the target neural cell population comprises a cannula.

10. The method of claim 1, wherein the nucleotide sequence is operably linked to a cell type-specific promoter.

11. The method of claim 1, wherein the light-responsive opsin polypeptide is a channelrhodopsin-2 polypeptide derived from *Chlamydomonas rheinhardtii*.

12. The method of claim 1, wherein the light-responsive opsin polypeptide is a channelrhodopsin polypeptide derived from *Volvox carteri*.

13. The method of claim 8, wherein the nucleic acid is a viral vector.

14. The method of claim 1, wherein the target neural cell population is in the motor cortex, the anterior thalamus, or the posterior thalamus.

15. The method of claim 1, wherein the light source is an optical fiber.

* * * * *